US009833212B2

(12) United States Patent
Nagae et al.

(10) Patent No.: US 9,833,212 B2
(45) Date of Patent: Dec. 5, 2017

(54) IMAGE PROCESSING DEVICE AND X-RAY DIAGNOSTIC APPARATUS

(71) Applicant: TOSHIBA MEDICAL SYSTEMS CORPORATION, Otawara-shi (JP)

(72) Inventors: Ryoichi Nagae, Nasushiobara (JP); Satoru Ohishi, Otawara (JP); Yuichiro Watanabe, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 92 days.

(21) Appl. No.: 14/944,715

(22) Filed: Nov. 18, 2015

(65) Prior Publication Data
US 2016/0143605 A1    May 26, 2016

(30) Foreign Application Priority Data

Nov. 21, 2014    (JP) .................................. 2014-236698

(51) Int. Cl.
| G06T 7/00 | (2017.01) |
| A61B 6/00 | (2006.01) |
| G06T 11/60 | (2006.01) |
| G06T 5/50 | (2006.01) |

(52) U.S. Cl.
CPC .......... *A61B 6/5211* (2013.01); *A61B 6/4441* (2013.01); *A61B 6/463* (2013.01); *A61B 6/481* (2013.01); *A61B 6/487* (2013.01); *A61B 6/504* (2013.01); *G06T 5/50* (2013.01); *G06T 11/60* (2013.01); *A61B 6/542* (2013.01); *G06T 2207/10116* (2013.01); *G06T 2207/20224* (2013.01); *G06T 2207/30104* (2013.01)

(58) Field of Classification Search
CPC .. G06T 5/50; G06T 7/20; G06T 7/254; G06T 7/97; G06T 11/60; G06T 2207/20224; G06T 2207/30104; A61B 6/481; A61B 6/486; A61B 6/487; A61B 6/504; A61B 6/5211

See application file for complete search history.

(56) References Cited

U.S. PATENT DOCUMENTS

| 2009/0016587 A1* | 1/2009 | Strobel et al. ................ 382/130 |
| 2009/0110252 A1* | 4/2009 | Baumgart et al. ............ 382/130 |
| 2010/0329523 A1 | 12/2010 | Ostermeier et al. .......... 382/128 |
| 2013/0077839 A1* | 3/2013 | Horz et al. .................... 382/130 |

FOREIGN PATENT DOCUMENTS

| JP | 2007-94022 A | 4/2007 | ............. G02B 27/22 |
| JP | 2013-233227 A | 11/2013 | ............... A61B 6/00 |

* cited by examiner

*Primary Examiner* — Andrew W Johns
(74) *Attorney, Agent, or Firm* — Oblon, McClelland, Maier & Neustadt, L.L.P.

(57) ABSTRACT

According to one embodiment, an image processing device includes processing circuitry. The processing circuitry acquires a plurality of first image data indicating a plurality of time-sequential bloodstream images obtained after administering contrast agent to an object, and sets a target region on second image data. The second image data are generated based on the plurality of the first image data so as to indicate information on temporal change of pixel values of each pixel. Further, the processing circuitry selects a reproduction section by selecting at least reproduction-start image data and reproduction-end image data from the plurality of first image data based on bloodstream information of the target region.

15 Claims, 15 Drawing Sheets

IMAGE PROCESSING DEVICE AND X-RAY DIAGNOSTIC APPARATUS

CROSS-REFERENCE TO RELATED APPLICATIONS

This application claims the benefit of priority of Japanese Patent Application No. 2014-236698, filed Nov. 21, 2014, the entire contents of which are incorporated herein by reference.

FIELD

Embodiments described herein relate generally to an image processing device and an X-ray diagnostic apparatus.

BACKGROUND

As a technique of obtaining bloodstream information inside a patient body, fluoroscopic imaging with the use of contrast agent and an X-ray diagnostic apparatus is known. As an example of fluoroscopic imaging, DSA (Digital Subtraction Angiography) images are generated by time-sequentially imaging the same region of a patient using an X-ray diagnostic apparatus before and after administration of contrast agent.

Specifically, subtraction images corresponding to respective time phases obtained by subtracting a mask image from a contrast image of each time phase imaged after administration of contrast agent are defined as DSA images. The above-described mask image means an X-ray image imaged before administration of contrast agent used as a reference, and the above-described contrast image means an X-ray image in which contrast agent is depicted. Since blood vessels dyed by contrast agent are selectively depicted in DSA images by eliminating shade and shadow unnecessary for observing blood vessels, DSA images are useful for diagnosis of blood vessels.

When a doctor diagnoses a blood vessel disease such as cerebral arteriovenous malformation and dural arteriovenous fistula, a blood vessel image useful for diagnosis cannot be obtained only from DSA images in some cases. To be concrete, it becomes difficult in some cases to specify or distinguish a blood vessel through which contrast agent flows into a lesion area.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Figure 1:
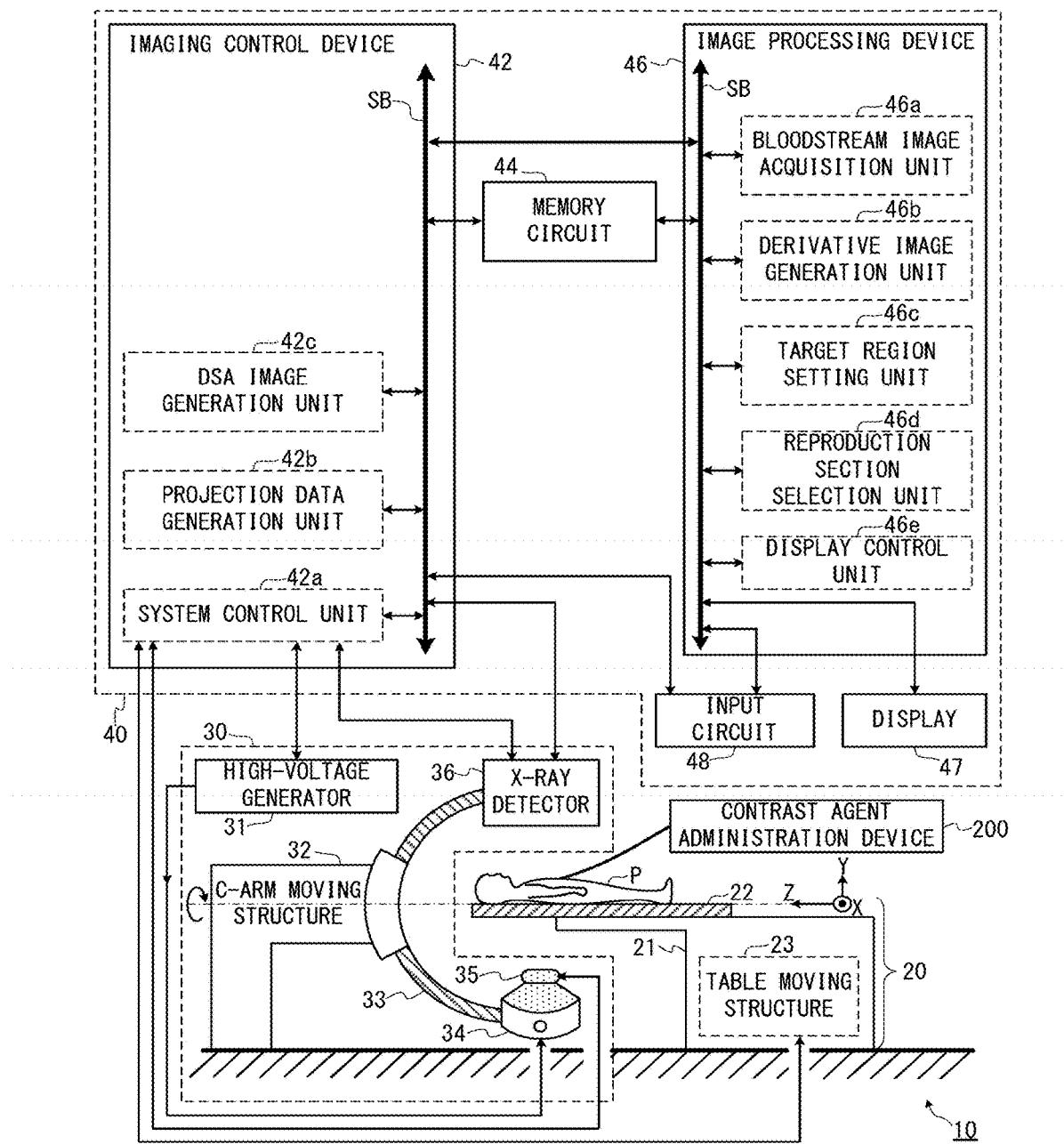
FIG. 1 is a block diagram showing an example of configuration of an X-ray diagnostic apparatus of the present embodiment.

An X-ray diagnostic apparatus can reproduce DSA images like a moving picture by time-sequentially and continuously displaying the DSA images. However, DSA images in which blood flow of a target region such as a therapeutic region is clearly depicted are, for example, only several percent of the DSA images of all the time phases. Thus, in order to enable visual confirmation of blood flow of a target region easily and effectively, it is desirable that only the DSA images clearly depicting blood flow of the target region are reproduced and the rest of the DSA images are not reproduced.

In terms of the above-described point, configuration in which a starting time phase and an ending time phase of a reproduction section are selected by a user's manipulation out of the DSA images of all the time phases is possible. However, manipulation for a user is complicated in this configuration.

For the above reason, in the embodiment described below, the reproduction section of DSA images is automatically selected by an image processing device installed inside an X-ray diagnostic apparatus, so that the DSA images clearly depicting blood flow of the target region are included. This technical idea of automatically selecting the reproduction section of DSA images does not exist in conventional technology, and the method of this automatic selection will be explained by reference to g FIG. 6 to FIG. 8 as described below.

Moreover, while time-sequentially displaying DSA images in one region of a screen, derivative images of these DSA images are time-sequentially displayed in parallel in another region of the screen for the purpose of providing satisfactory observation of blood flow of the target region in the following embodiment. In examples of the following embodiment, the derivative images of DSA images are parametric time phase images of multiple time phases generated based on temporal change of each pixel value of DSA images and are color images each of which distinguishably depicts blood flow from a perspective different from DSA images. Methods of generating parametric time phase images will be explained in detail by reference to FIG. 2 to FIG. 5 as described below.

Hereinafter, embodiments of the present invention will be explained with reference to the accompanying drawings. Note that the same reference numbers are given for identical components in each figure, and duplicate explanation is omitted.

In general, according to one embodiment, an image processing device includes processing circuitry. The processing circuitry acquires a plurality of first image data indicating a plurality of time-sequential bloodstream images obtained after administering contrast agent to an object, and sets a target region on second image data. The second image data are generated based on the plurality of the first image data so as to indicate information on temporal change of pixel values of each pixel. Further, the processing circuitry selects a reproduction section by selecting at least reproduction-start image data and reproduction-end image data from the plurality of first image data based on bloodstream information of the target region.

<Configuration of X-Ray Diagnostic Apparatus>

FIG. 1 is a block diagram showing an example of configuration of the X-ray diagnostic apparatus 10 of the present embodiment. As an example here, components of the X-ray diagnostic apparatus 10 will be explained by classifying them into three groups: a bed device 20, an X-ray generation/detection system 30, and a computing system 40.

Firstly, the bed device 20 includes a supporting platform 21, a table 22, and a table moving structure 23 disposed inside the supporting platform 21. An object P is loaded on the table 22. As an example here, a contrast agent administration device 200 is set on the object P.

The supporting platform 21 supports the table 22 in such a manner that the table 22 can move in the horizontal direction (i.e. the Z axis direction of the apparatus coordinate system). The table moving structure 23 positions an imaging region of the object P between an X-ray detector 36 and a diaphragm device 35 described below, by moving the table 22 in the Z axis direction of the apparatus coordinate system under control of a system control unit 42a of the computing system 40 described below.

As an example here, the above-described apparatus coordinate system, whose X axis, Y axis and Z axis are perpendicular to each other, is defined as follows.

First, the Y axis direction is defined as the vertical direction, and the table 22 is disposed at such a position that the direction of the normal line of its top surface accords with the Y axis direction. The horizontal moving direction of the table 22 is defined as the Z axis direction, and the table is disposed in such a manner that its longitudinal direction becomes equal to the Z axis direction. The X axis direction is the direction perpendicular to these Y axis direction and Z axis direction.

Secondly, the X-ray generation/detection system 30 includes a high-voltage generator 31, a C-arm moving structure 32, a C-arm 33, an X-ray tube 34, the diaphragm device 35, and the X-ray detector 36.

The C-arm 33 is an arm which supports the X-ray tube 34, the diaphragm device 35, and the X-ray detector 36. The X-ray detector 36 and the pair of the X-ray tube 34 and the diaphragm device 35 are arranged by the C-arm 33 so as to face each other with the object P interposed therebetween.

The C-arm moving structure 32 rotates and moves the C-arm 33 according to the imaging region, under the control of the system control unit 42a.

The high-voltage generator 31 generates high voltage and supplies the X-ray tube 34 with the generated high voltage.

The X-ray tube 34 generates X-rays by using the high voltage supplied from the high-voltage generator 31.

The diaphragm device 35 narrows down an irradiation range of X-rays by, for example, sliding diaphragm blades so that the imaging region of the object P is selectively irradiated with X-rays, and controls the irradiation range by adjusting degree of opening of the diaphragm blades.

The X-ray detector 36 includes, for example, many of non-illustrated X-ray detection elements arrayed in a matrix for converting X-rays into electric signals. The X-ray detector 36 converts X-rays having passed through the object P into electric signals to accumulate these electric signals by using these X-ray detection elements, and outputs the accumulated electric signals to the projection data generation unit 42b described below.

Thirdly, the computing system 40 includes an imaging control device 42, a memory circuit 44, an image processing device 46, a display 47, and an input circuit 48. Since main characteristics of the X-ray diagnostic apparatus 10 are functions of the image processing device 46, hereinafter, functions of the image processing device 46 will be explained after briefly explaining functions of other components in advance.

The imaging control device 42 controls an imaging operation of the X-ray diagnostic apparatus 10. The imaging control device 42 includes the system control unit 42a, the projection data generation unit 42b, a DSA image generation unit 42c, and a system bus SB as communication wiring interconnecting these components.

The system control unit 42a controls the entirety of the X-ray diagnostic apparatus 10 in setting of imaging conditions, imaging operations, and display processing.

The projection data generation unit 42b generates projection data of X-ray images by using electric signals converted from the X-rays having passed through the object P by the X-ray detector 36. The projection data generation unit 42b stores the generated projection data in the memory circuit 44.

The DSA image generation unit 42c acquires projection data of an X-ray image before administration of contrast agent (i.e. image data of a mask image) and projection data of X-ray images of respective time phases after the administration of contrast agent from the memory circuit 44. Thereby, the DSA image generation unit 42c generates image data of DSA images of the respective time phases by calculating subtraction between the projection data of the mask image and the projection data of the X-ray image of each time phase after the administration of contrast agent. The DSA image generation unit 42c stores the image data of the DSA images in the memory circuit 44.

The above-described projection means, for example, to depict a three-dimensional object in a two-dimensional image, the above-described projection data means image data of a two-dimensional image. Although "image data" includes image data of a three-dimensional image and image data of a two-dimensional image in a broad sense, "image data" does not include image data of a three-dimensional image in a narrow sense. For distinction in the present specification, image data of a two-dimensional image are referred to as image data, and image data of a three-dimensional image are referred to as volume data. In order to simplify the explanation in the following examples, examples of two-dimensional images will be explained first.

The display 47 performs image display, display of a setting screen of imaging conditions, display of a setting screen of image processing conditions, and the like.

The input circuit 48 includes a keyboard, operation buttons, and the like, in order for a user to input various commands such as imaging conditions and image processing conditions. The input circuit 48 transfers the inputted contents to the system control unit 42a and the image processing device 46.

The image processing device 46 generates a series of time-sequential parametric time phase images based on temporal change of each pixel value of DSA images, and causes the display 47 to display the DSA images and the parametric time phase images in parallel.

The above-described parametric imaging means, for example, processing of forming a color image or gray-scale image from a single parameter or plural parameters. In a broad sense, the parametric imaging includes projection data of an X-ray image generated by the projection data generation unit 42b. This is because a pixel value of each pixel in projection data of an X-ray image indicates a value of X-ray transmissivity as a parameter.

In a narrow sense, the parametric imaging means processing of generating a color image by calculating bloodstream information parameter values except X-ray transmissivity for each pixel based on projection data of X-ray images. In the present embodiment, the parametric imaging in the narrow sense will be explained. In the following explanation, an image generated by the parametric imaging in the narrow sense is referred to as a parametric image, and each of time-sequential color images generated from one parametric image is referred to as a parametric time phase image. Generation methods of parametric images and parametric time phase images will be explained below.

The image processing device 46 includes a bloodstream image acquisition unit 46a, a derivative image generation unit 46b, a target region setting unit 46c, a reproduction section selection unit 46d, a display control unit 46e, and a system bus SB as communication wiring interconnecting these components.

The bloodstream image acquisition unit 46a acquires image data of time-sequential DSA images obtained by fluoroscopic imaging on the same object P before and after administration of contrast agent, from the memory circuit 44.

The derivative image generation unit 46b acquires bloodstream information parameter values for parametric imaging for each pixel, based on temporal change of each pixel value corresponding to the same region of the object P in image data of each DSA image (see FIG. 2 to be described below).

Here, each pixel, whose position is common to all the time-sequential DSA images, belongs to the common region of the object P, and a bloodstream information parameter value is calculated for each pixel of the DSA images. The derivative image generation unit 46b generates image data of a parametric image having the same pixel number as the pixel number of each DSA image so that each pixel of the parametric image corresponds to the pixel of each DSA image at the same position and a chromatic color based on the bloodstream information parameter value of each pixel of the DSA images is assigned to each pixel of the parametric image. The image data of a parametric image are image data in which each pixel has three pixel values for red, green, and blue as three primary colors, for example. The derivative image generation unit 46b generates image data of time-sequential parametric time phase images from one parametric image.

The target region setting unit 46c sets a target region common to all the parametric time phase images obtained from the time-sequential DSA images.

Since a case where image size (i.e. number of rows and columns in pixel) of each of DSA images, a parametric image, and parametric time phase images is common to will be explained as an example in the embodiment below, pixels whose row number and column number are both common to each other indicate the same region of the object P. Thus, a target region being set on each of parametric time phase images are also set on DSA images at the same position as each parametric time phase image in the example of the present embodiment.

The reproduction section selection unit 46d acquires pixels value of respective pixels of the same region as the target region, from the image data of the DSA images of all the time phases. On the basis of bloodstream information on the target region obtained from temporal change of a pixel value of each of these pixels, the reproduction section selection unit 46d selects image data of consecutive DSA images, each of which clearly depicts blood flow of the target region, out of the DSA images of all the time phases as a reproduction section. The above-described "consecutive" means time phases of the respective DSA images of the reproduction section become a sequential number.

For example, the reproduction section selection unit 46d selects a reproduction section by selecting at least image data corresponding to a starting time phase of reproduction (i.e., reproduction-start image data) and image data corresponding to an ending time phase of reproduction (i.e., reproduction-end image data). In this selection processing, the reproduction section selection unit 46d may select data of sequential images corresponding to all of the respective time phases between the starting time phase of reproduction and the ending time phase of reproduction including these starting and ending time phases of reproduction.

In addition, the reproduction section selection unit 46d may output information on image data selected for selecting a reproduction section, so as to store this information in the memory circuit 44, an image processing server of a PACS (Picture Archiving and Communication System), and the like. When the reproduction section selection unit 46d outputs information on image data selected for selecting a reproduction section, the outputted information on image data includes information on starting and ending time phases of the selected reproduction section or information on all the time phases included in the selected reproduction section, for example.

The above-described information on time phases means, for example, image data corresponding to each time phase, information on frame number associated with the image data corresponding to each time phase, time information associated with the image data corresponding to each time phase, and a combination of these types of information.

In this case, the reproduction section selection unit 46*d* can acquire the information on image data selected for selecting a reproduction section from the memory circuit 44 or the image processing server of a PACS at an arbitrary timing after imaging the object P according to an instruction from a user via the input circuit 48, for example. Thus, a reproduction section can be easily selected and DSA images of the selected reproduction section can be time-sequentially displayed on the display 47 at an arbitrary timing after imaging the object P. At this time, if image data are not included in the information on image data outputted by the reproduction section selection unit 46*d*, the display 47 may acquire image data of DSA images corresponding to the reproduction section from the memory circuit 44 or the image processing server of a PACS.

The display control unit 46*e* controls the display 47, so that the display 47 continuously and time-sequentially displays the DSA images in the reproduction section on one region of its screen while displaying the parametric time phase images on another region of the screen continuously and time-sequentially.

Principle of Present Embodiment

Figure 2:
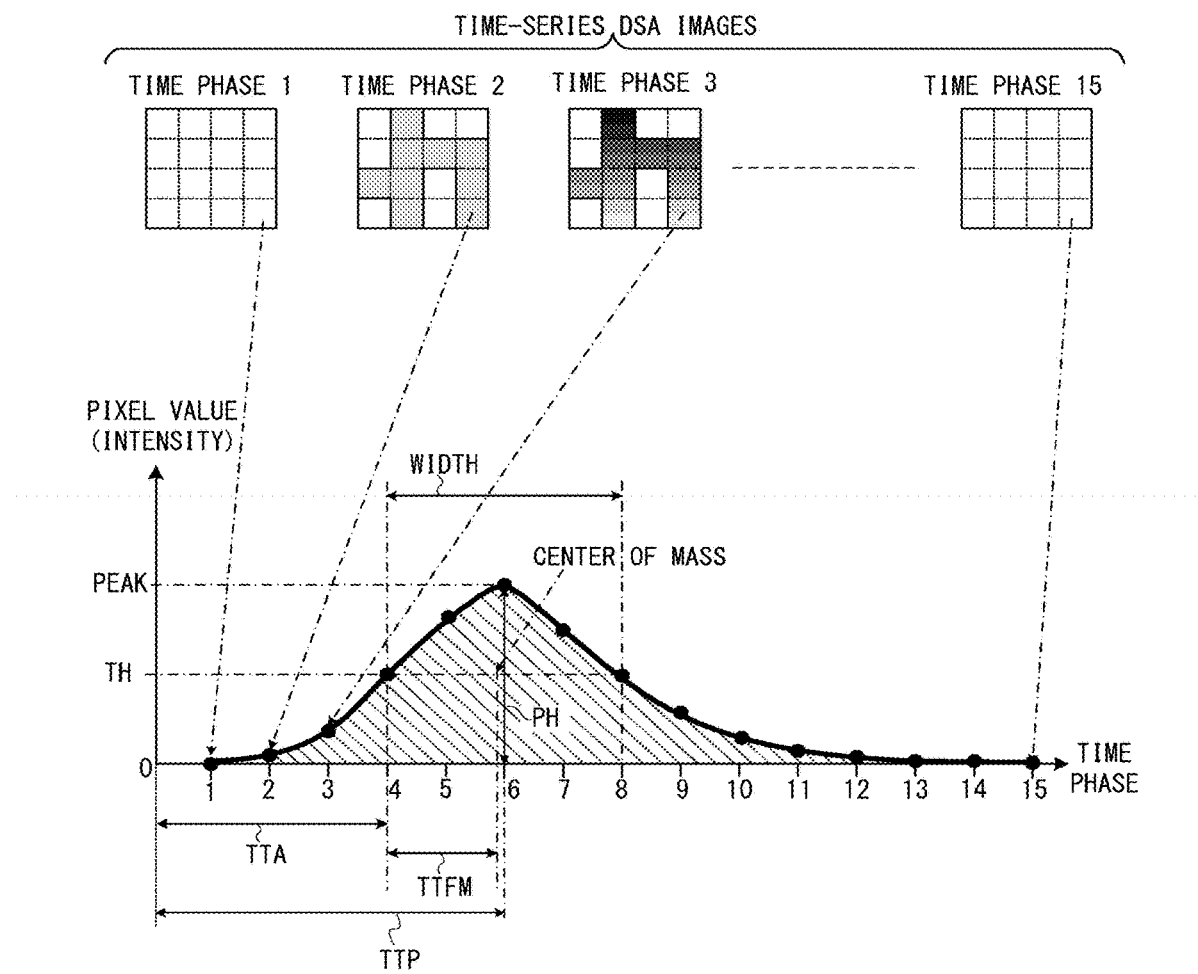
FIG. 2 is a schematic diagram showing a method of calculating temporal change of contrast agent concentration, as an example of a method of acquiring bloodstream information parameter values in a generation process of parametric images.

FIG. 2 is a schematic diagram showing a method of calculating temporal change of contrast agent concentration, as an example of a method of acquiring bloodstream information parameter values in a generation process of a parametric image. The upper part of FIG. 2 shows DSA images of respective time phases, and the lower part of FIG. 2 shows an example of temporal change of contrast agent concentration targeting one pixel. Although an example in which pixel number is 4×4 is shown in the upper part of FIG. 2, this is only an example for simplifying the explanation and the pixel number may be larger than 4×4 (the same holds true for each of FIG. 3 to FIG. 5).

For example, consider a case where imaging is performed before and after administration of contrast agent by the X-ray diagnostic apparatus 10 so that projection data of sixteen X-ray images for the same region of the same object P in the order of time t=0 before the administration, time t=1, 2, 3, 4, . . . and 15 after the administration are generated by the projection data generation unit 42*b*.

In this case, image data of fifteen DSA images (subtraction images) corresponding to t=1, 2, 3, 4, . . . and 15 can be obtained by subtracting the X-ray image at t=0 (mask image) from each of the fifteen X-ray images after the administration (see the upper part of FIG. 2). Incidentally, in the upper part of FIG. 2, t=1 is defined as the time phase 1, t=2 is defined as the time phase 2 (the same hereinafter).

Here, the derivative image generation unit 46*b* calculates temporal change of contrast agent concentration for each pixel by calculating pixel value change over the fifteen time-sequential DSA images from the time phases 1 to 15 for each pixel whose position is common to the fifteen DSA images. The lower part of FIG. 2 shows an example of temporal change of contrast agent concentration targeting one pixel positioned at the bottom-right corner in each DSA image (whose pixel number is 4×4 in this example). In the lower part of FIG. 2, the vertical axis indicates contrast agent concentration (i.e., intensity of contrast agent) and the horizontal axis indicates time phase (i.e., elapsed time t).

More specifically, the X-ray absorption rate of the contrast agent is higher than that of human tissues. Thus, exposure dose of an X-ray detection element corresponding to the position of the object P, where the contrast agent concentration is high, becomes lower, and the contrast agent in such a position of the object P is more darkly projected in an X-ray image than its peripheral regions.

Additionally, each pixel value of each DSA image is a difference value from the pixel value of the same position of the mask image. Thus, if one pixel of the same position is focused on and appropriate processing such as sign inversion is performed on time phase change of the pixel values of this pixel, the result becomes equivalent to temporal change of the contrast agent concentration.

As bloodstream information parameters used for parameter images, for example, TTP (Time To Peak), PH (Peak Height), TTA (Time To Arrival), WIDTH, TTFM (Time To First Moment), and AUC (Area Under Curve) corresponding to square measure of the diagonally right down shadow region in the lower part of FIG. 2 are included (see the lower part of FIG. 2).

TTP indicates at which time phase contrast agent concentration reaches its peak.

PH indicates a peak value of contrast agent concentration.

AUC indicates a time integration value of contrast agent concentration from the first time phase to the final time phase of DSA images.

TTA is the time phase (clock time) when contrast agent concentration first exceeds a threshold value TH in the temporal change curve of contrast agent concentration.

As an example in the lower part of FIG. 2, a case where the threshold value TH is 50% of the peak value is shown. However, 50% of the peak value is only an example of the threshold value TH and the threshold value TH is not limited to this value. For example, the threshold value TH may be 30%, 40%, or 60% of the peak value.

WIDTH is a period (i.e., time interval) during which contrast agent concentration is higher than the threshold value TH.

TTFM is a period (i.e., time interval) from the timing of TTA to the center of mass with respect to the time integration value of contrast agent concentration (integrated from the first time phase to the final time phase).

Figure 3:
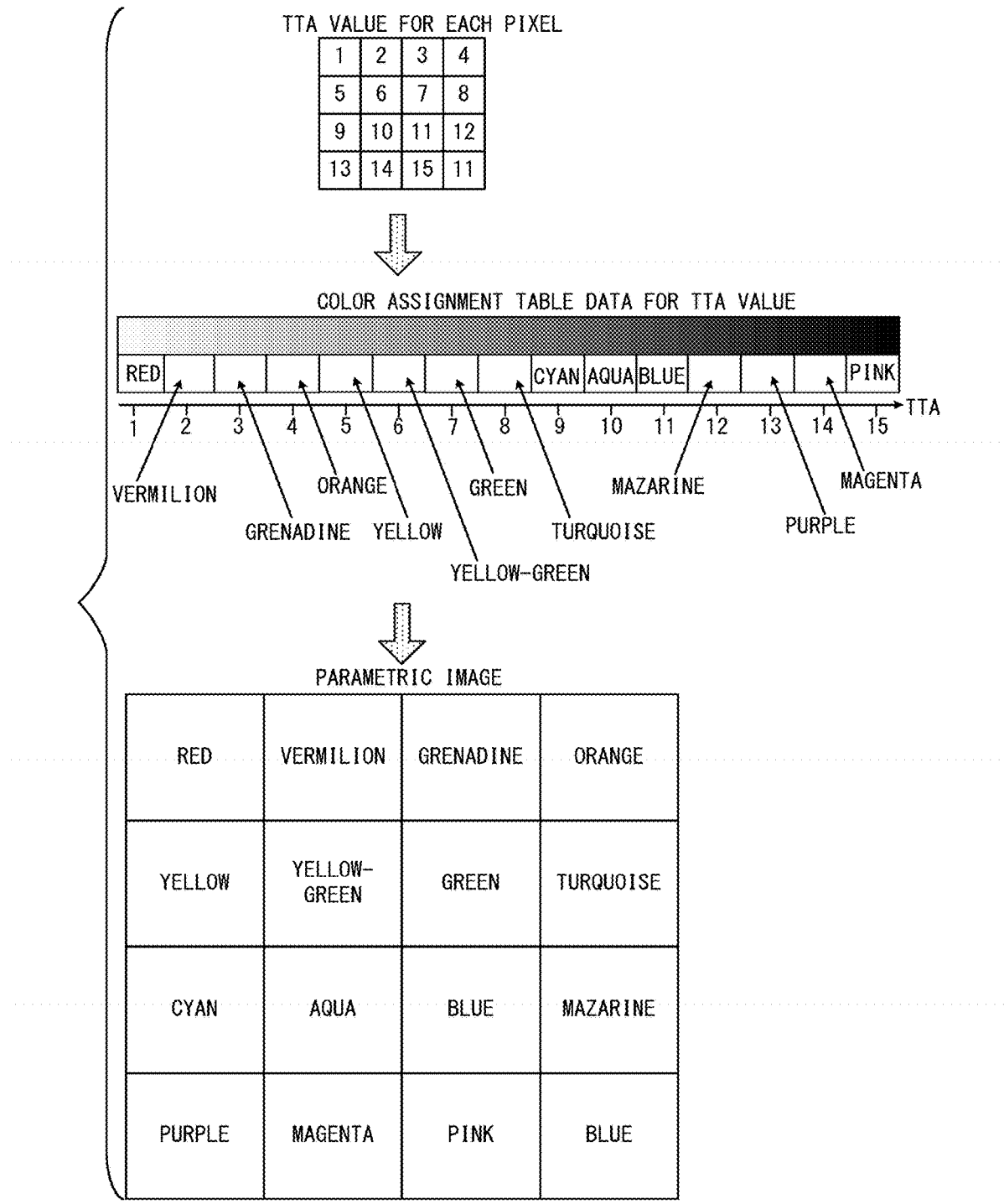
FIG. 3 is a schematic diagram showing an example of a method of generating a parametric image whose parameter is TTA (Time To Arrival)

FIG. 3 is a schematic diagram showing an example of a method of generating a parametric image whose parameter is TTA. The top part of FIG. 3 shows an example of calculated TTA values for each pixel whose position is common to all the frames of DSA images, under the premise that pixel number is 4×4 as an example. The middle part of FIG. 3 shows an example of color-assignment table data for TTA stored in the derivative image generation unit 46*b*.

As an example here, red is assigned for each pixel whose TTA value is 1, vermilion is assigned for each pixel whose TTA value is 2, grenadine is assigned for each pixel whose TTA value is 3, orange is assigned for each pixel whose TTA value is 4, yellow is assigned for each pixel whose TTA value is 5, yellow-green is assigned for each pixel whose TTA value is 6, green is assigned for each pixel whose TTA value is 7, turquoise is assigned for each pixel whose TTA value is 8, cyan is assigned for each pixel whose TTA value is 9, aqua is assigned for each pixel whose TTA value is 10, blue is assigned for each pixel whose TTA value is 11, mazarine is assigned for each pixel whose TTA value is 12, purple is assigned for each pixel whose TTA value is 13, magenta is assigned for each pixel whose TTA value is 14, and pink is assigned for each pixel whose TTA value is 15.

Although the color-assignment table data are illustrated by a horizontal gray-scale bar in the middle part of FIG. 3 for convenience, the color-assignment table data actually give different chromatic colors for respective parameter values. This is because it is difficult to distinguish each blood vessel region from its peripheral regions and thus it is desirable that various colors including chromatic colors are assigned to respective pixels. However, note that method of assigning color to each pixel is not limited to the above-described method and other methods may be used.

Although three pixel values of red, green, and blue as three primary colors are used for each pixel in the example of the above-described color assignment, embodiments of the present invention is not limited to such an aspect. For example, color may be assigned to each pixel so that one or two of a red value, a green value, and a blue value is/are commonly zero for all the pixels.

Additionally, the derivative image generation unit 46b may store the color-assignment table data as table data in which a set of a red value, a green value, and a blue value in predetermined bit notation as three primary color values is given for each TTA value. For example, in the case of eight bit notation, (255, 0, 0) as a set of a red value, a green value, and a blue value is assigned to 1 as a TTA value.

The bottom part of FIG. 3 shows color of each pixel defined by the TTA value of each pixel in the top part of FIG. 3 and the color assignment table in the middle part of FIG. 3. In other words, an image whose pixels are displayed by the respective colors shown in the bottom part of FIG. 3 is a parametric image whose bloodstream information parameter is TTA.

Additionally, the derivative image generation unit 46b also stores color assignment table for other bloodstream information parameters such as color assignment table for TTP and color assignment table for PH. Although a parametric image is generated based on TTA as a parameter in the above-described example, a parametric image may be generated based on TTP or PH as a parameter.

As mentioned above, the derivative image generation unit 46b generates image data of one parametric image for a series of time-sequential DSA images.

Next, the derivative image generation unit 46b generates image data of multiple time-sequential parametric time phase images from image data of one parametric image. This point is another characteristic of the present embodiment and will be explained by reference to FIG. 4 and FIG. 5 as follows.

Figure 4:
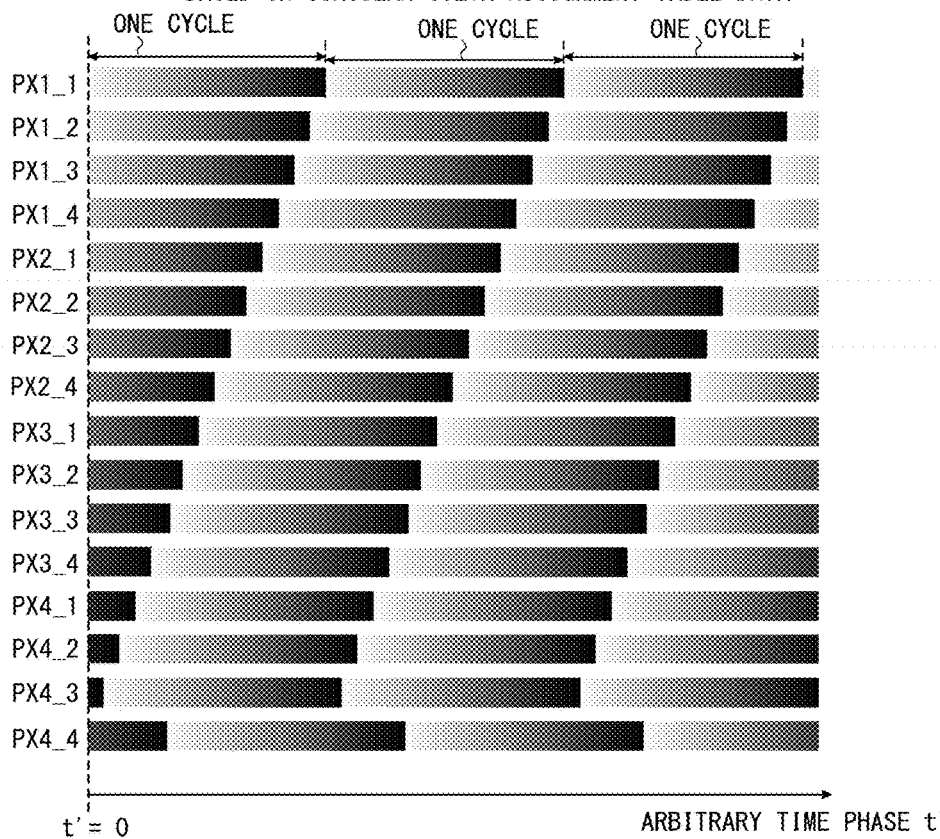
FIG. 4 is a schematic diagram showing an example of circular color-assignment table data used for generating parametric time phase images.

FIG. 4 is a schematic diagram showing an example of circular color-assignment table data used for generating parametric time phase images.

The upper part of FIG. 4 is the same parametric image as the bottom part of FIG. 3, the lower part inside the frame of each pixel shows color of the parametric image, and the upper part inside the frame of each pixel shows the position of its pixel in row and column. In the upper part inside the frame of each pixel, the last letter indicates column number and the third letter from the last indicates row number. Thus, the symbol of the pixel in the first column of the first row is described as PX1_1, the symbol of the pixel in the second column of the first row is described as PX1_2, the symbol of the pixel in the third column of the first row is described as PX1_3, and the same applies hereinafter.

The lower part of FIG. 4 is a schematic diagram showing color of each pixel, which continuously changes along with elapse of arbitrary time phase t' based on the circular color-assignment table data. Although the circular color-assignment table data are illustrated by gray-scale for convenience in the lower part of FIG. 4, the circular color-assignment table data are actually configured of continuously changing chromatic colors. The circular color-assignment table data give a chromatic color which changes continuously and periodically along with elapse of arbitrary time phase t', for example, in the order of red, vermilion, grenadine, orange, yellow, yellow-green, green, turquoise, cyan, aqua, blue, mazarine, purple, magenta, pink, red, and so forth.

Parametric time phase images are equal to its original parametric image in vertical pixel number and horizontal pixel number, and are generated by continuously changing the color of each pixel of the parametric image according to the circular color-assignment table data. As an example here, the parametric time phase image at arbitrary time phase t'=0 (the first time phase) is the same as the parametric image.

The pixel number of the parametric image is sixteen in this example. Thus, when TTA values are different from one pixel to another in this parametric image, sixteen colors different from each other are assigned to the respective sixteen pixels of the parametric time phase image at arbitrary time phase t'=0. Additionally, when plural pixels are equal to each other in TTA value, plural pixels whose colors are common to each other exist in the parametric time phase image at arbitrary time phase t'=0. In the example of the upper part of FIG. 4, the pixel in the third column of the third row is equal in TTA value to the pixel in the fourth column of the fourth row, and thus these two pixels show a common color in parametric time phase images at every arbitrary time phase.

The derivative image generation unit 46b stores various types of circular color-assignment table data, each type is different in color at the first arbitrary time phase from other types but length of one cycle is aligned and is common to every type. For example, in the case of the pixel PX1_1, its TTA value is one and its color in the parametric image is red. Thus, the derivative image generation unit 46b selects the circular color-assignment table data starting from red for the pixel PX1_1, and determines the color of the pixel PX1_1 of a parametric time phase image at each arbitrary time phase t' based on the selected circular color-assignment table data.

In the case of the pixel PX1_2, its TTA value is two and thus its color in the parametric image is vermilion. Thus, the derivative image generation unit 46b selects the circular color-assignment table data starting from vermilion for the pixel PX1_2, and determines the color of the pixel PX1_2 of a parametric time phase image at each arbitrary time phase t' based on the selected circular color-assignment table data.

The derivative image generation unit 46b determines color of each of other pixels in a parametric time phase image of at each arbitrary time phase t' in a similar manner as described above. In this manner, the derivative image generation unit 46b generates image data of time-sequential parametric time phase images, by sequentially changing color of each pixel based on the circular color-assignment table data which give consecutive color change.

Here, arbitrary time phase t' is a concept different from time phase of DSA images. Since DSA images are images obtained by subtracting the mask image from each of time-sequential X-ray images after administration of contrast agent, time phase of each of time-sequential DSA images corresponds to imaging time t of each of time-sequential X-ray images after administration of contrast agent. Thus, time phase of DSA images can be precisely defined based on elapsed time from the timing of administration of contrast agent by defining the timing of administration of contrast agent as t=0, for example. However, arbitrary time phase t' of each of parametric time phase images does not correspond to imaging time t of each of time-sequential X-ray images.

Specifically, the derivative image generation unit 46b can generate one hundred parametric time phase images for one cycle by assigning one hundred arbitrary time phases from t'=0 to t'=99 within one cycle of the circular color-assignment table data, and can also generate ten parametric time phase images for one cycle by assigning ten arbitrary time phases within one cycle of the circular color-assignment table data. Since assignment of time phases in generating parametric time phase images is arbitrary, time phase of a parametric time phase image is described as an arbitrary time phase (virtual time phase) t'.

Figure 5:
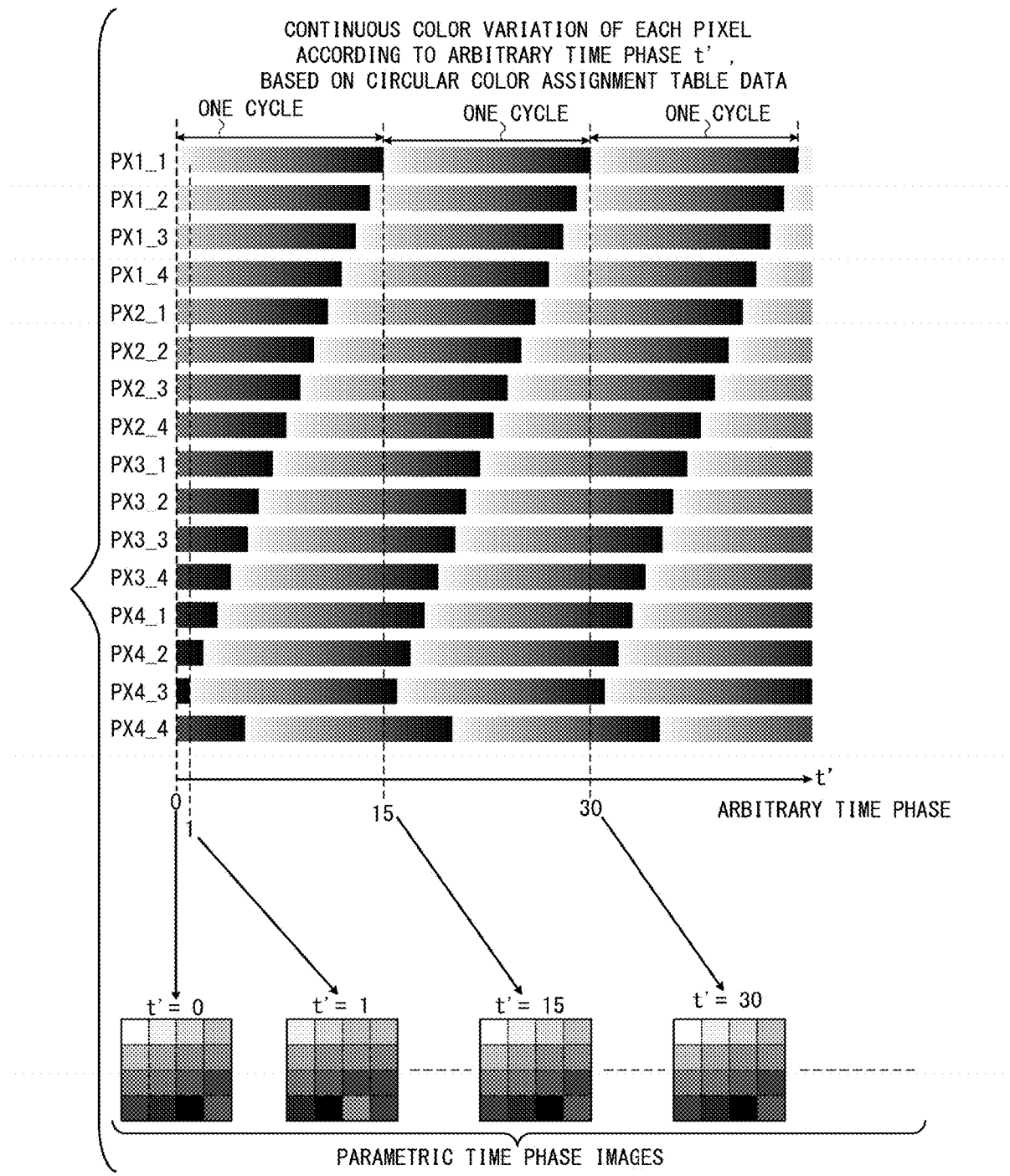
FIG. 5 is a schematic diagram showing parametric time phase images generated by assigning fifteen arbitrary time phases (from t'=0 to t'=14) to one cycle of the circular color-assignment table data shown in FIG. 4 as an example of explaining arbitrary time phases.

FIG. 5 is a schematic diagram showing parametric time phase images generated by assigning fifteen arbitrary time phases (from t'=0 to t'=14) to one cycle of the circular color-assignment table data shown in FIG. 4, as an example of explaining arbitrary time phases.

Here, color of each pixel of each parametric time phase image changes along with elapse of arbitrary time phase t' and length of one cycle determined by the circular color-assignment table data is common to all the pixels. Therefore, as to generation of necessary image data of parametric time phase images, it is enough to generate image data of parametric time phase images whose number is the same as the number of arbitrary time phases assigned to one cycle of the circular color-assignment table data. This is because a parametric time phase image at a certain arbitrary time phase t'=α is the same as the parametric time phase image whose arbitrary time phase is one cycle later than the arbitrary time phase t'=α.

Since fifteen arbitrary time phases are assigned to one cycle of the circular color-assignment table data in the example of FIG. 5, the parametric time phase image at the arbitrary time phase t'=0 is the same as the parametric time phase image at each of the arbitrary time phases t'=15 and t'=30.

Thus, the derivative image generation unit 46b generates image data of a series of parametric time phase images corresponding to one cycle of the circular color-assignment table data, and transfers the generated image data to the display control unit 46e. The display control unit 46e can display the parametric time phase images like a moving picture which eternally continues, by repeating the processing of time-sequentially reproducing these parametric time phase images on the display 47.

Next, though a position of a target region is important in selecting DSA images each of which clearly depicts blood flow of the target region (i.e., automatic selection of the reproduction section), there are two cases for setting the target region. One is the case where the target region is set by a user's manipulation via the input circuit 48, and the other is the case where the target region is automatically set by the target region setting unit 46c. The method of automatically setting a target region by the target region setting unit 46c is another characteristic of the present embodiment, and it will be explained by reference to FIG. 6 and FIG. 7 as follows.

Figure 6:
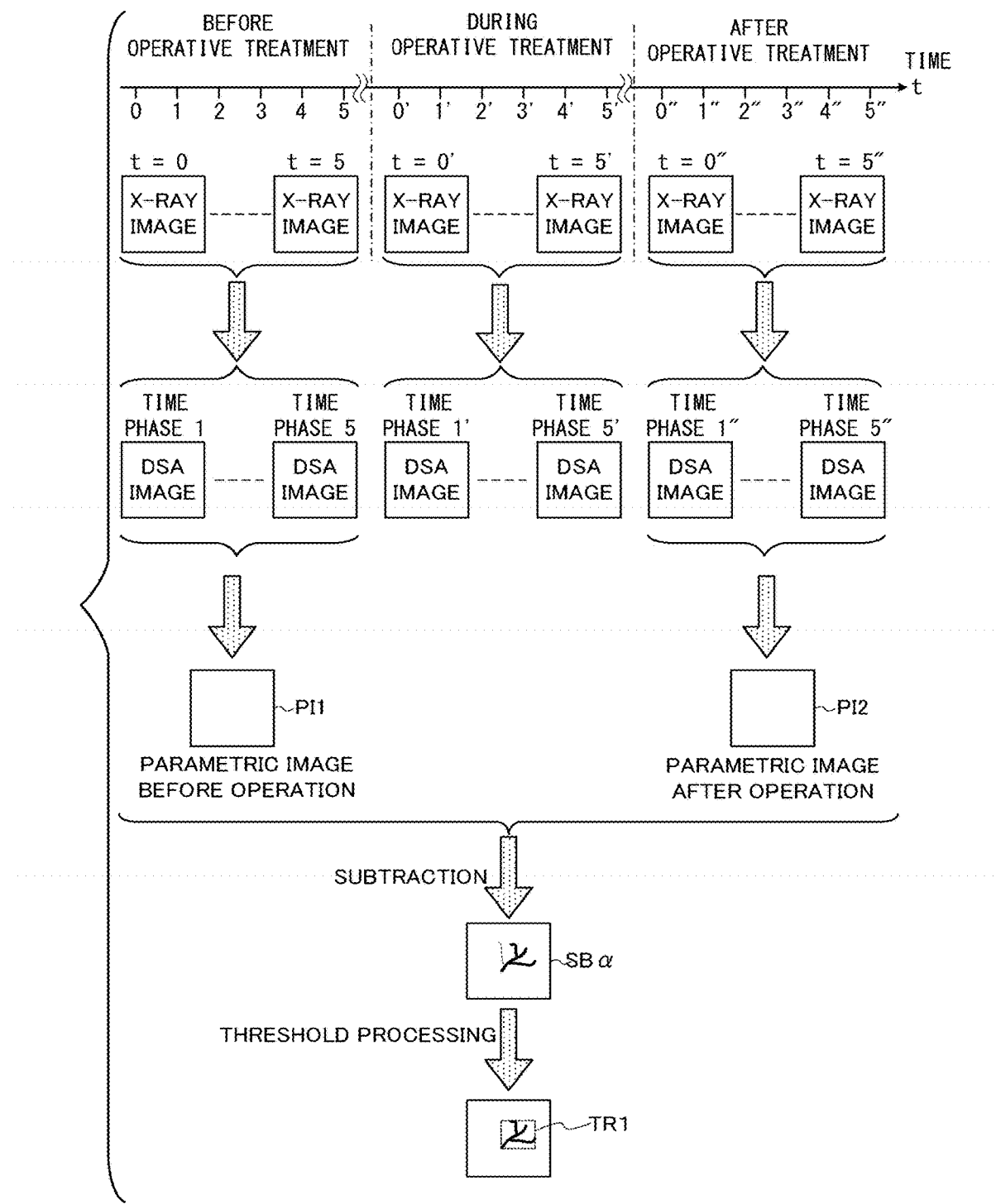
FIG. 6 is a schematic diagram showing an example of a method of setting a target region based on derivative images obtained from time-sequentially imaged X-ray images.

FIG. 6 is a schematic diagram showing an example of a method of setting a target region based on derivative images obtained from time-sequentially imaged X-ray images.

Figure 7:
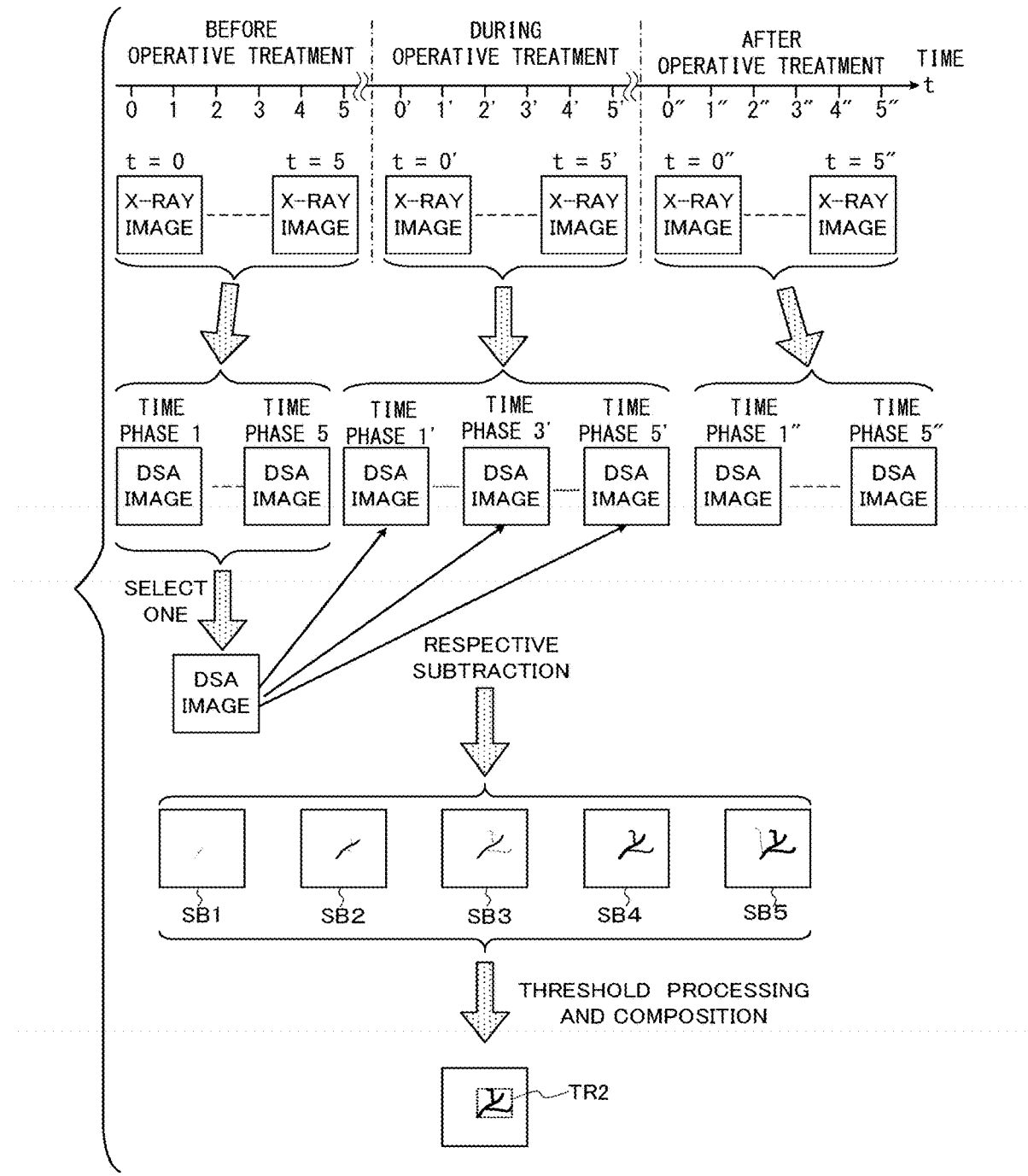
FIG. 7 is a schematic diagram showing another example of a method of setting a target region based on derivative images obtained from time-sequentially imaged X-ray images.

FIG. 7 is a schematic diagram showing another example of a method of setting a target region based on derivative images obtained from time-sequentially imaged X-ray images.

In the top part of each of FIG. 6 and FIG. 7, the horizontal axis indicates imaging time t.

For example, it is assumed that the same region of the same object P is time-sequentially imaged before and after administration of contrast agent prior to a vasodilatation operation. In other words, it is assumed that a mask image is imaged and contrast agent is administered at the same time of t=0 and five X-ray images (i.e., contrast images) are imaged from t=1 to t=5 at equal intervals. As an example in the present specification, it is assumed that a contrast image is an X-ray image imaged after administration of contrast agent without being subjected to image processing using another image.

Next, after dissipation of the effect of the contrast agent administered at t=0, it is assumed that the same region of the same object P is time-sequentially imaged before and after readministration of contrast agent during the operative treatment. In other words, it is assumed that a mask image is imaged and contrast agent is administered again at the same time of t=0' and five X-ray images (i.e., contrast images) are imaged from t=1' to t=5' at equal intervals.

Moreover, after dissipation of the effect of the contrast agent administered again at t=0', it is assumed that the same region of the same object P is time-sequentially imaged before and after the third administration of contrast agent, subsequent to the operative treatment. In other words, it is assumed that a mask image is imaged and contrast agent is administered again at the same time of t=0" and five X-ray images (i.e., contrast images) are imaged from t=1' to t=5' at equal intervals.

The top part of each of FIG. 6 and FIG. 7 shows this state.

Then, five preoperative DSA images of time phases 1 to 5, each of which corresponds to each of imaging time t=1, t=2, t=3, t=4, and t=5, are generated by subtracting the mask image at time t=0 before the administration of contrast agent from each of the contrast images from imaging time t=1 to t=5 after the administration of contrast agent, in a manner similar to FIG. 2.

Similarly, five DSA images of time phases 1' to 5' during the operative treatment, each of which corresponds to each of imaging time t=1', t=2', t=3', t=4', and t=5', are generated by subtracting the mask image at time t=0' before the readministration of contrast agent from each of the contrast images from imaging time t=1' to t=5' after the readministration of contrast agent.

Similarly, five postoperative DSA images of time phases 1" to 5", each of which corresponds to each of imaging time t=1", t=2", t=3", t=4", and t=5", are generated by subtracting the mask image at time t=0" before the third administration of contrast agent from each of the contrast images from imaging time t=1" to t=5" after the third administration of contrast agent.

The second top part of FIG. 6 shows this state.

Afterward, in the example of FIG. 6, bloodstream information parameters such as TTA as an example are calculated on the basis of temporal change of each pixel value of the five preoperative DSA images from the time phases 1 to 5, and a preoperative parametric image PI1 is generated. In a similar manner, a postoperative parametric image PI2 is generated on the basis of the five postoperative DSA images from the time phases 1" to 5".

The third top part of FIG. 6 shows this state.

The target region setting unit 46c generates a parametric subtraction image SBα by subtracting each pixel value of the preoperative parametric image PI1 from each pixel value of the postoperative parametric image PI2, in such a manner that each subtraction is performed between pixels at the same position.

The fourth top part of FIG. 6 shows this state.

The target region setting unit 46c extracts a pixel region, in which each pixel value is equal to or higher than a threshold value, from the parametric subtraction image SBα as a region of changed bloodstream by performing threshold processing on the parametric subtraction image SBα.

The target region setting unit 46c calculates the minimum rectangular region which includes the region of changed bloodstream as a target region TR1, for example. Additionally, the target region setting unit 46c may set the target region TR1 to a region obtained by expanding the minimum rectangular region which includes the region of changed bloodstream by 110% in the vertical direction and horizontal direction. The above expansion ratio is only an example of a concrete expansion ratio value and should not be interpreted as limiting the present embodiment.

The bottom part of FIG. 6 shows this state.

Incidentally, the target region TR1 is not limited to a rectangular region but it may be set as another shape such as a circle and a hexagon.

In addition, in the case of a vasodilatation operation, a region of changed bloodstream is a region where blood flow is improved, and can be extracted by performing threshold processing on the subtraction image obtained by subtracting the preoperative parametric image PI1 from the postoperative parametric image PI2 in a manner as described above. By contrast, in the case of an embolization operation, the region of changed bloodstream is a region where blood flow is occluded and it can be extracted by performing threshold processing on the subtraction image obtained by subtracting the postoperative parametric image PI2 from the preoperative parametric image PI1 in a similar manner as described above.

Moreover, images used for determining the target region TR1, i.e., images used for extracting a region of changed bloodstream are not limited to the parametric images PI1 and PI2 before and after the operative treatment.

For example, a region of changed bloodstream may be extracted by performing threshold processing on a subtraction image between one of five postoperative DSA images of time phases 1" to 5" and one of preoperative DSA images of time phases 1' to 5' in a similar manner as described above, and then the target region TR1 may be determined based on the extracted region of changed bloodstream.

Furthermore, the target region TR1 may be determined by using a subtraction image between a peak trace image generated from DSA images of all the preoperative time phases and another peak trace image generated from DSA images of all the postoperative time phases, in a similar manner as described above.

The above-described peak trace image means, for example, an image in which every pixel has a pixel value at the time phase of its Peak Height, obtained based on temporal change of a pixel value over all the time phases for each pixel whose position is common to the DSA images of all the time phases (see the lower part of FIG. 2). In other words, a peak trace image is an image which indicates a blood vessel region by luminance level of the maximum pixel value of each pixel therein.

Additionally, the target region TR1 may be determined by using a subtraction image between one of the five preoperative contrast images from imaging time t=1 to t=5 and one of the five postoperative contrast image from imaging time t=1" to t=5" in a similar manner as described above.

Moreover, a subtraction image used for determining the target region TR1 may be generated, on the basis of not only images having been imaged before and after the operative treatment and their derivative images but also images having been imaged during the operative treatment.

For example, the first subtraction image may be generated by subtracting the preoperative parametric image PI1 from a parametric image during the operative treatment generated from the five DSA images of the time phases 1' to 5'.

Next, the second subtraction image may be generated by subtracting the above-described parametric image during the operative treatment from the postoperative parametric image PI2. Then, the target region may be determined so that the target region includes a composition region obtained by composing (a) the region of the first subtraction image in which every pixel value is equal to or higher than the threshold value and (b) the region of the second subtraction image in which every pixel value is equal to or higher than the threshold value.

As another example, the target region setting unit 46c can determine a target region TR2, by determining the process of temporally changing bloodstream during the operative treatment based on each subtraction image between one of the preoperative DSA images and each of the DSA images during the operative treatment, as shown in FIG. 7.

Specifically, for example, the target region setting unit 46c selects one DSA image in which blood vessels are the most extensively depicted, out of all the preoperative DSA images. Next, the target region setting unit 46c generates subtraction images SB1, SB2, SB3, SB4, SB5 by subtracting the selected preoperative DSA image from each of the five DSA images of all the time phases 1' to 5' during the operative treatment.

The third top part of FIG. 7 shows this state.

Since the subtraction image SB1 indicates difference between the selected preoperative DSA image and the DSA image of the time phases 1' at which only a little time elapses from the start of the operative treatment, the region of changed bloodstream is not clearly depicted in the subtraction image SB1.

By contrast, since the subtraction image SB3 indicates difference between the selected preoperative DSA image and the DSA image of the time phases 3' at which a certain amount of time elapses from the start of the operative treatment, the region of changed bloodstream is depicted to a certain degree in the subtraction image SB3.

Moreover, since the subtraction image SB5 indicates difference between the selected preoperative DSA image and the DSA image of the time phases 5' which is close to the end of the operative treatment, the region of changed bloodstream is prominently depicted in the subtraction image SB5.

For the above reasons, the target region setting unit 46c extracts the region of changed bloodstream, in which every pixel value is equal to or higher than the threshold value, from each of the subtraction images SB1 to SB5 by performing common threshold processing on each of them. Then, the target region setting unit 46c calculates a composition region of the five regions of changed bloodstream extracted from the five subtraction images SB1 to SB5. The target region setting unit 46c can determine the minimum rectangular region including this composition region as the target region TR2, for example.

The bottom part of FIG. 7 shows this state.

Next, a method of determining a reproduction section of DSA images based on the target region will be explained. This point is another characteristic of the present embodiment, and is explained by reference to FIG. 8.

Figure 8:
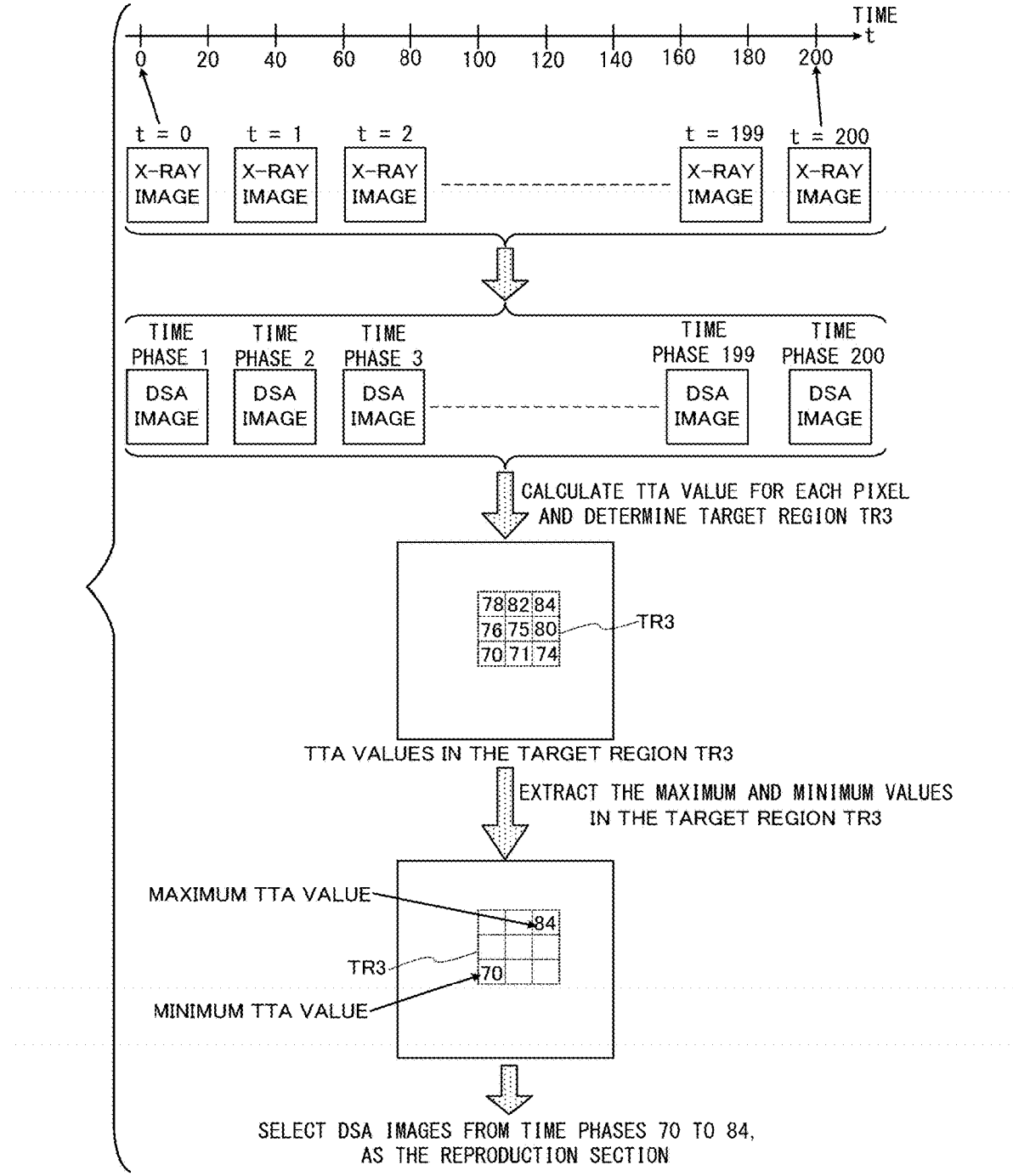
FIG. 8 is a schematic diagram showing an example of a method of automatically selecting a reproduction section of DSA images executed by a reproduction section selection unit.

FIG. 8 is a schematic diagram showing an example of a method of automatically selecting a reproduction section of DSA images executed by the reproduction section selection unit 46d. In the top part of FIG. 8, the horizontal axis indicates imaging time t. As an example here, it is assumed that a total of 201 X-ray images are imaged from imaging time t=0 before administration of contrast agent to imaging time t=200 and the imaging time t=1 to the imaging time t=200 are after administration of contrast agent. The top part of FIG. 8 shows this state.

In this case, 200 DSA images corresponding to the respective time phases 1 to 200 are generated in a similar manner as described above. The second top part of FIG. 8 shows this state.

Afterward, a bloodstream information parameter for generating a parametric image is calculated for each pixel whose position is common to all the DSA images, based on temporal change of each pixel value of all the DSA images in a similar manner as described above. As an example here, it is assumed that TTA is calculated as a bloodstream information parameter.

Then, a target region TR3 is selected by the target region setting unit 46c as explained with FIG. 7. The reproduction section selection unit 46d acquires a bloodstream information parameter of each pixel of the target region TR3. The third top part of FIG. 8 shows this state.

The reproduction section selection unit 46d extracts the minimum TTA value and the maximum TTA value of the target region TR3, for example (see the bottom part of FIG. 8). The reproduction section selection unit 46d determines the earliest time phase of TTA of all the pixels in the target region TR3 indicated by the minimum TTA value, as the starting time phase of the reproduction section. Similarly, the reproduction section selection unit 46d determines the latest time phase of TTA of all the pixels in the target region TR3 indicated by the maximum TTA value, as the ending time phase of the reproduction section.

In other words, the reproduction section selection unit 46d selects the DSA images between two time phases corresponding to the respective minimum and maximum TTA values in the target region TR3, as the reproduction section as an example here.

The above-described "select the DSA images between two time phases as the reproduction section" means to select at least two DSA images corresponding to respective two time phases, and includes selecting all the DSA images between two time phases. For instance, when a reproduction section is selected by selecting DSA images corresponding to at least respective two time phases as reproduction-start image data and reproduction-end image data, in the example of FIG. 8, a reproduction section is selected by selecting two DSA images corresponding to respective time phases 70 and 84. Additionally, when all the DSA images between two time phases are selected as a reproduction section, in the example of FIG. 8, the fifteen DSA images from the time phases 70 to 84 are selected as the reproduction section.

Incidentally, a reproduction section may be selected by using another bloodstream information parameter such as TTP which changes according to bloodstream arrival time, instead of the TTA values of all the pixels in the target region TR3 for the following reason. As long as the selected DSA images are between two time phases corresponding to the respective minimum and maximum values of a bloodstream information parameter reflecting bloodstream arrival time within the target region, blood vessels of the target region are more clearly depicted in the selected DSA images than the non-selected DSA images of all the time phases.

Note that selection of a period between two time phases corresponding to the respective minimum and maximum values of a bloodstream information parameter in a target region is only an example of a method of selecting a reproduction section. To be more precise, since TTP is a peak value as an example, the time phase slightly prior to the time phase of the minimum TTP value within the target region is considered to be the time phase at which contrast agent flows into the target region. Thus, in the example of FIG. 8, the reproduction section selection unit 46d may select a period between the time phase slightly prior to the time phase of the minimum TTA value in the target region TR3 and the time phase slightly subsequent to the time phase corresponding to the maximum TTA value in the target region TR3, as the reproduction section. The same holds true for other bloodstream information parameters such as TTP.

In other words, the reproduction section selection unit 46d may select a reproduction section by selecting the following two DSA images. One of the two DSA images corresponds to the time phase slightly prior to the time phase at which a TTA value in the target region TR3 becomes its minimum value. The other of the two DSA images corresponds to the time phase slightly subsequent to the time phase at which a TTA value in the target region TR3 becomes its maximum value. In addition, the reproduction section selection unit 46d may output information on image data selected for selecting a reproduction section, so as to store this information in the memory circuit 44, an image processing server of a PACS, and the like.

Display Aspect of Present Embodiment

Figure 9:
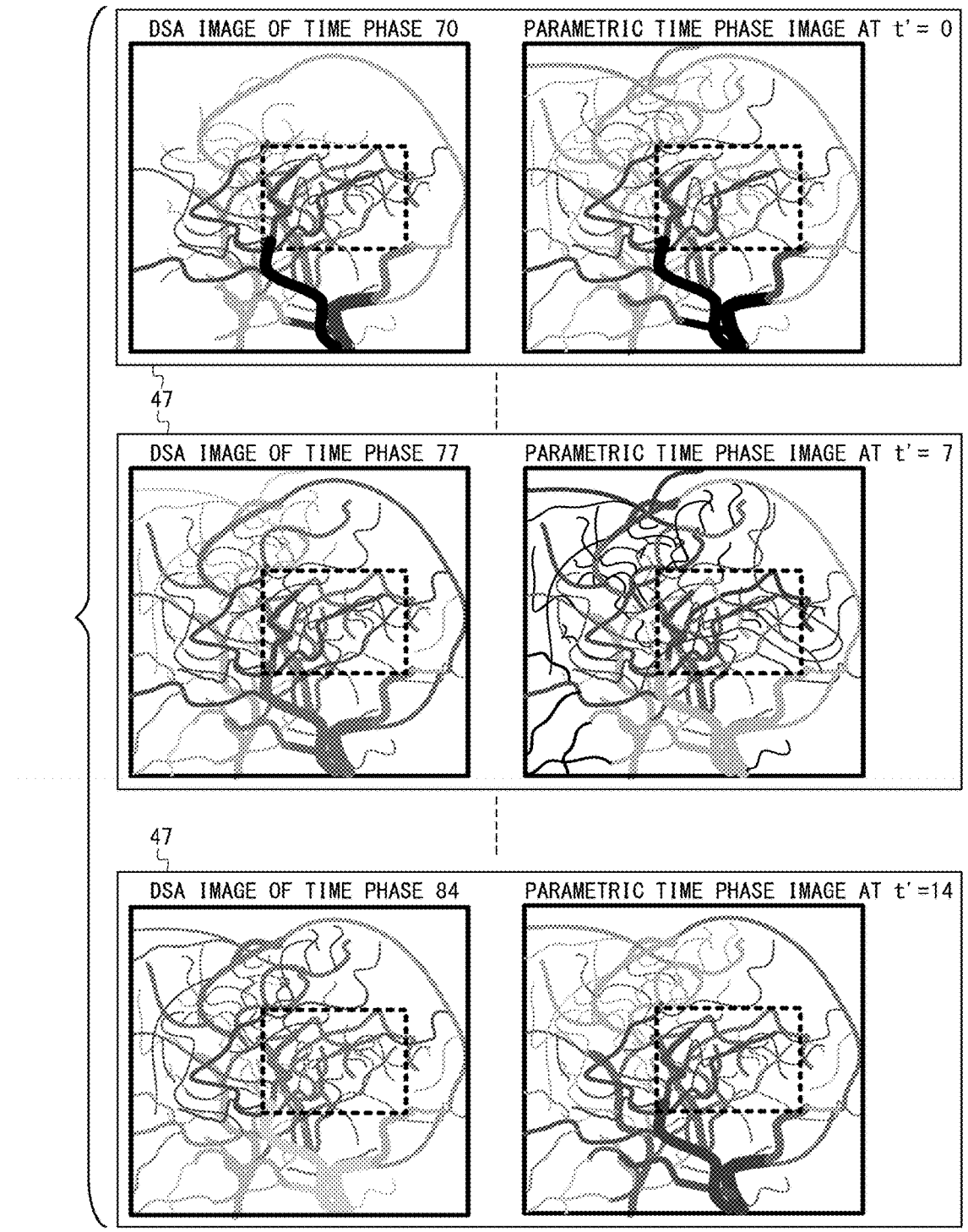
FIG. 9 is a schematic diagram showing the first example of a display aspect of time-sequentially reproducing DSA images of the reproduction section and parametric time phase images in parallel.

FIG. 9 is a schematic diagram showing the first example of a display aspect of time-sequentially reproducing DSA images of the reproduction section and parametric time phase images in parallel. As shown in FIG. 9, under the control of the display control unit 46e, the display 47 time-sequentially reproduces the DSA images of the automatically selected reproduction section on the left half of its screen, while time-sequentially reproducing parametric time phase images of one cycle on the right half of the screen, for example.

As an example here, it is assumed that DSA images of the time phases 70 to 84 are selected as the reproduction section like the example in FIG. 8 and fifteen parametric time phase images are generated for one cycle length like the example of FIG. 5.

As an example here, the display control unit 46e controls the frame rate of reproducing DSA images and parametric time phase images, so that all the parametric time phase images of one cycle are time-sequentially displayed in one cycle during which all the DSA images of the reproduction section are time-sequentially displayed.

In other words, fifteen parametric time phase images from the arbitrary time phases t'=0 to t'=14 are sequentially displayed on the right side of the display 47 in a period during which fifteen DSA images of the time phases 70 to 84 are sequentially displayed on the left side of the display 47. As to a case where parametric time phase images of plural cycles are displayed in a display period of DSA images of the reproduction section, it will be explained by reference to FIG. 13 as described below.

The top part of FIG. 9 shows a display state in which the DSA image of the time phase 70 and the parametric time phase image of the arbitrary time phase t'=0 are displayed in parallel on the display 47 at the starting time of reproducing the DSA images of the reproduction section.

The middle part of FIG. 9 shows a display state in which the DSA image of the time phase 77 and the parametric time phase image of the arbitrary time phase t'=7 are displayed in parallel on the display 47 at the intermediate time point of reproducing the DSA images of the reproduction section.

The bottom part of FIG. 9 shows a display state in which the DSA image of the time phase 84 and the parametric time phase image of the arbitrary time phase t'=14 are displayed in parallel on the display 47 at the ending time of reproducing the DSA images of the reproduction section.

Since a DSA image is a subtraction image between a mask image and a contrast image, each pixel of a DSA image has only one pixel value equivalent to a value of luminance level. Thus, each DSA image is displayed not in full color but in gray-scale, for example.

As shown in the top part of FIG. 9, in the first DSA image of the reproduction section, lower regions are shown by darker gray scale due to contrast agent and some blood vessels outside the target region are not depicted.

As shown in the middle part of FIG. 9, in the DSA image of the intermediate time point of the reproduction section, lower regions are less darkly depicted due to outflow of contrast agent and some blood vessels which are not depicted in the first time phase of the reproduction section are depicted in the region above the target region.

As shown in the bottom part of FIG. 9, in the DSA image of the ending time phase of the reproduction section, lower regions are further brightly depicted due to further outflow of contrast agent.

By contrast, though parametric time phase images are shown by gray-scale in FIG. 9 for convenience, parametric time phase images are actually displayed in full color as explained with FIG. 3 to FIG. 5, for example. In other words, each pixel in one parametric time phase image has three luminance level values for the respective red, green, and blue as one set of pixel values, for example. A parametric time phase image has an advantage that an observer can easily visually follow not only a target region but also blood flow in the entire image by continuous color change.

Since full-color parametric time phase images having the above-described advantage are reproduced beside the DSA images of the reproduction section in a period during which these DSA images are sequentially displayed in gray-scale, it becomes easier for an observer to visually discriminate blood flow based on comparison between both.

Moreover, as an example in FIG. 9, the outer border of the target region determined by the target region setting unit 46c is surrounded by a bold broken-line frame and thereby the target region is distinguishably displayed in each DSA image and each parametric time phase image. Accordingly, visibility of the target region is improved and it becomes further easier for an observer to visually discriminate blood flow of the target region.

Since the number of the DSA images of the reproduction section is equal to the number of the parametric time phase images of one cycle in the above-described example, the frame rate of reproducing the parametric time phase images is controlled so that one parametric time phase image is displayed in a display period of one DSA images.

When the number of the DSA images of the reproduction section is different from the number of the parametric time phase images of one cycle, the display control unit 46e controls the display 47 so that all the parametric time phase images of one cycle are sequentially displayed in a period of sequentially displaying all the DSA images of the reproduction section. For example, when the number of the parametric time phase images of one cycle is twice the number of the DSA images of the reproduction section, the display control unit 46e controls the frame rate of reproducing parametric time phase images, so that two parametric time phase images are sequentially displayed in a period of displaying one DSA image.

Incidentally, as to how to display plural images on one screen, FIG. 9 is only one aspect. For example, the DSA images of the reproduction section may be displayed on the upper half of the display 47 in parallel with displaying the parametric time phase images on the lower half of the display 47, according to the shape of the display 47. In addition, as to aspects of distinguishing a target region, FIG. 9 is only an example and other examples will be explained by reference to FIG. 10 to FIG. 12.

Figure 10:
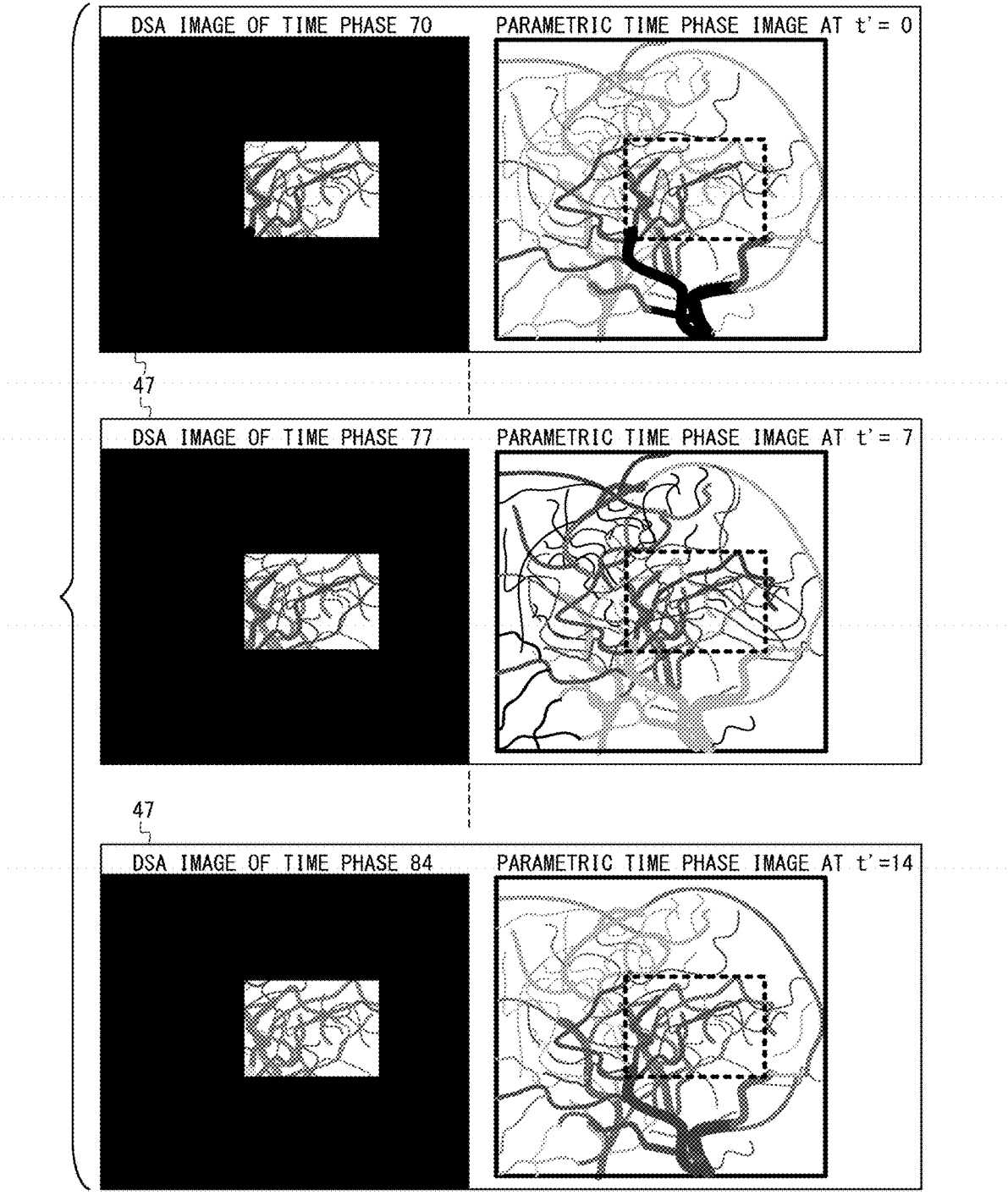
FIG. 10 is a schematic diagram showing the second example of the display aspect of time-sequentially reproducing DSA images of the reproduction section and parametric time phase images in parallel.

FIG. 10 is a schematic diagram showing the second example of the display aspect of time-sequentially reproducing the DSA images of the reproduction section and parametric time phase images in parallel. In FIG. 10, regions except the target region are masked by a uniform and fixed color such as black in display of DSA images on the left half of the display 47. Thereby, regions other than the target region are not displayed in the DSA images and thus it becomes easier to focus on observation of only the target region. The other points in FIG. 10 are the same as FIG. 9.

Figure 11:
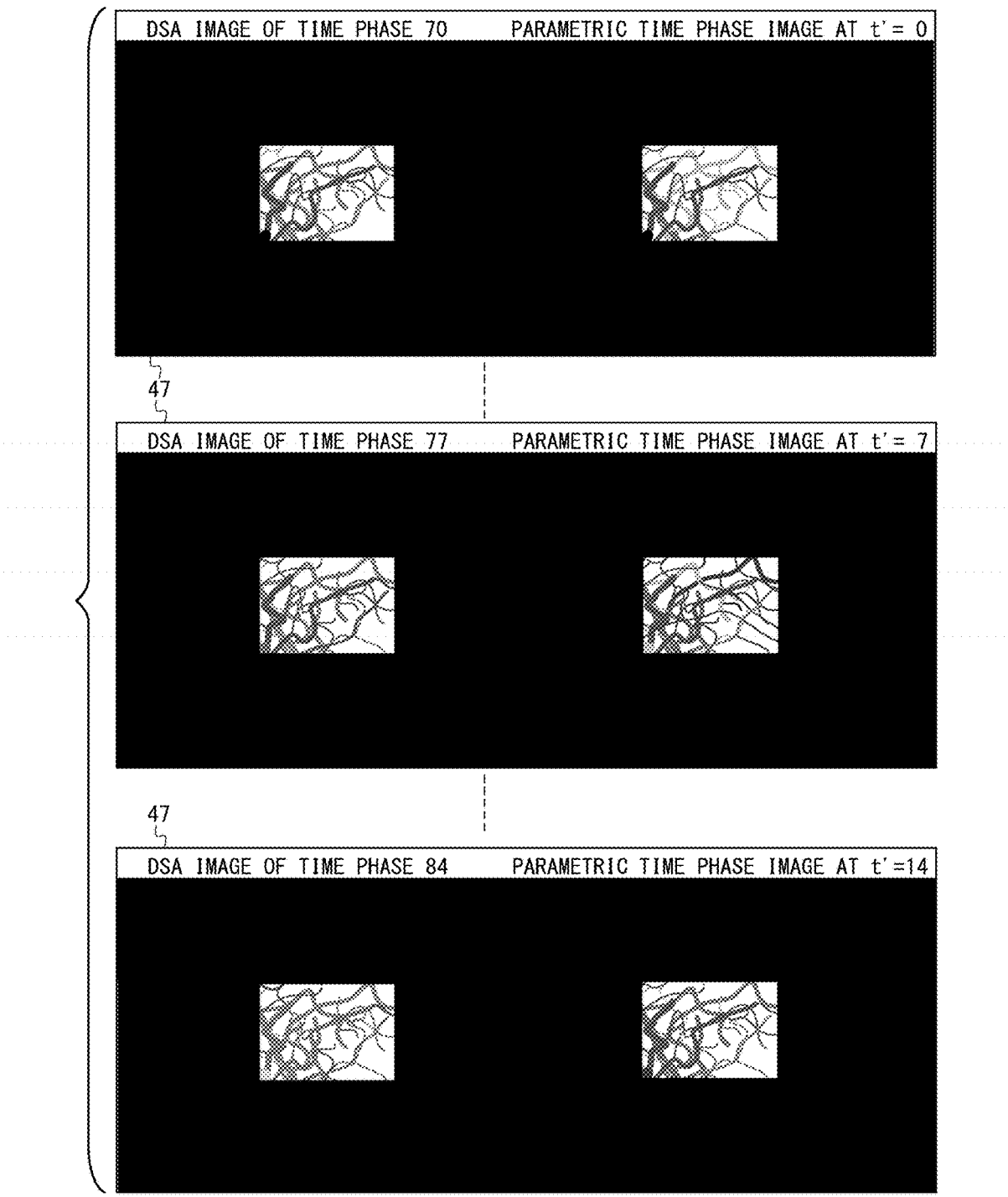
FIG. 11 is a schematic diagram showing the third example of the display aspect of time-sequentially reproducing DSA images of the reproduction section and parametric time phase images in parallel.

FIG. 11 is a schematic diagram showing the third example of the display aspect of time-sequentially reproducing DSA images of the reproduction section and parametric time phase images in parallel. In FIG. 11, regions except the target region are masked by a uniform and fixed color such as black not only in display of DSA images but also in display of parametric time phase images. Thereby, each target region in the DSA images and the parametric time phase images is distinguishably displayed. Other points in FIG. 11 are the same as FIG. 9.

Figure 12:
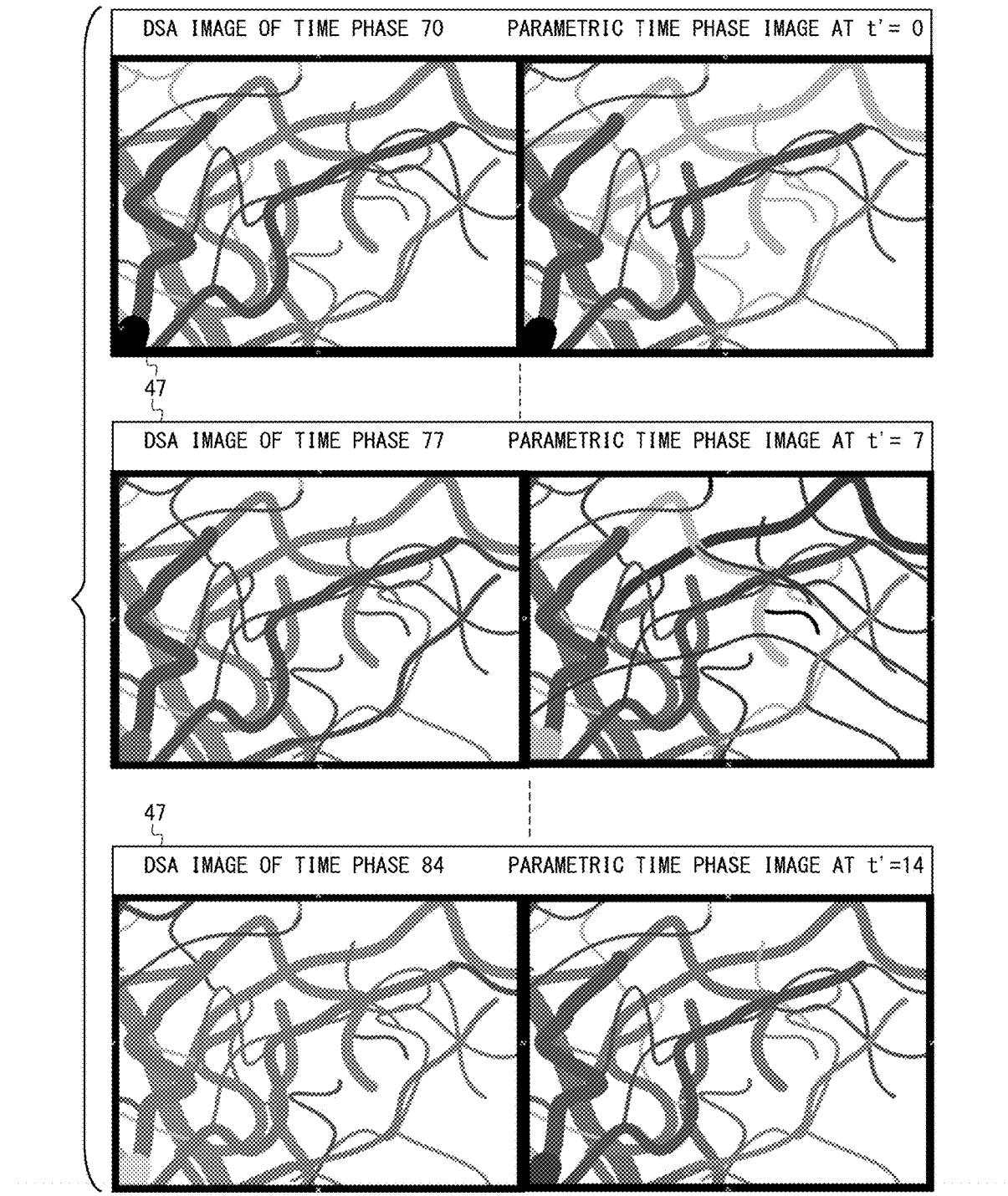
FIG. 12 is a schematic diagram showing the fourth example of the display aspect of time-sequentially reproducing DSA images of the reproduction section and parametric time phase images in parallel.

FIG. 12 is a schematic diagram showing the fourth example of the display aspect of time-sequentially reproducing the DSA images of the reproduction section and parametric time phase images in parallel. In FIG. 12, only the target region of each of the DSA images and the parametric time phase images is displayed. Furthermore, each target region is enlarged in display in FIG. 12 so that width of the composition image region obtained by connecting the border of the target region of the DSA image to the border of the target region of the parametric time phase image matches the width of screen of the display 47.

Although an example of a horizontally long screen is shown in FIG. 12, this is only an example of enlarged display. When the screen of the display 47 is vertically long, the display control unit 46e displays each target region of the DSA images on the upper half of the screen in parallel with display of each target region of the parametric time phase images on the lower half of the screen so that horizontal width of the screen matches the horizontal width of target region, for example.

Although parametric time phase images of one cycle are displayed in a display period of the DSA images of the reproduction section in the examples of the above FIG. 9 to FIG. 12, parametric time phase images of plural cycles may be sequentially displayed in a display period of the DSA images of the reproduction section.

Figure 13:
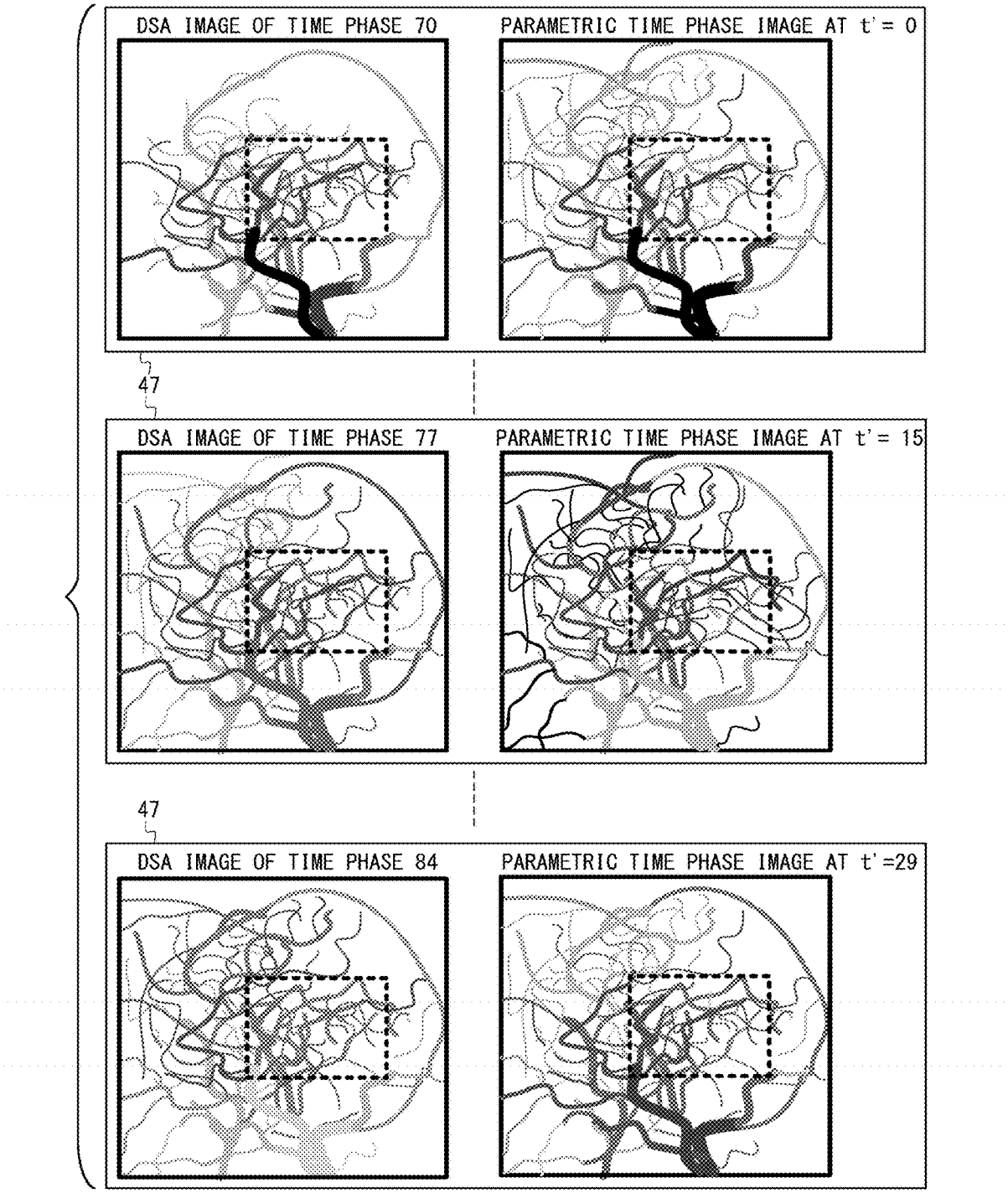
FIG. 13 is a schematic diagram showing an example of displaying parametric time phase images of two cycles in a display period of DSA images of the reproduction section.

FIG. 13 is a schematic diagram showing an example of displaying parametric time phase images of two cycles in a display period of DSA images of the reproduction section. FIG. 13 is the same as FIG. 9 except the frame rate of reproducing parametric time phase images.

Consider a case where the DSA images from time phases 70 to 84 are selected as the reproduction section in a manner similar to FIG. 9 and fifteen parametric time phase images are generated for one cycle length. In this case, in the example of FIG. 13, the display control unit 46e controls the reproduction frame rate so that thirty parametric time phase images from the arbitrary time phases t'=0 to t'=29 are displayed on the right side of the display 47 in a period during which the fifteen DSA images from the time phases 70 to 84 are displayed on the left side of the display 47.

The top part of FIG. 13 shows a display state in which the DSA image of the time phase 70 and the parametric time phase image of the arbitrary time phase t'=0 are displayed in parallel on the display 47 at the starting time of reproducing the DSA images of the reproduction section.

The middle part of FIG. 13 shows a display state in which the DSA image of the time phase 77 and the parametric time phase image of the arbitrary time phase t'=15 are displayed in parallel on the display 47 at the intermediate time point of reproducing the DSA images of the reproduction section. Since one cycle corresponds to a span from the arbitrary time phases t'=0 to t'=14, the arbitrary time phase t'=15 is the first image in the second cycle.

The bottom part of FIG. 13 shows a display state in which the DSA image of the time phase 84 and the parametric time phase image of the arbitrary time phase t'=29 are displayed in parallel on the display 47 at the ending time of reproducing the DSA images of the reproduction section. The above parametric time phase image of the arbitrary time phase t'=29 is the final image of the second cycle.

In each of the display aspects shown in FIG. 10 to FIG. 12, parametric time phase images of two cycles may be displayed in a display period of the DSA images of the reproduction section in a manner similar to the display example of FIG. 13.

Thus, when N DSA images whose time phases are consecutive are selected as the reproduction section, the number of parametric time phase images to be displayed in the period during which N DSA images are time-sequentially displayed is arbitrary such as N and triple of N.

Similarly, when N DSA images whose time phases are consecutive are selected as the reproduction section, the number of cycles of parametric time phase images to be displayed in the period during which N DSA images are time-sequentially displayed is arbitrary. In other words, three cycles, four cycles, or more than four cycles of parametric time phase images may be displayed during the display period of the DSA images of the reproduction section, for example.

Operation of Present Embodiment

Figure 14:
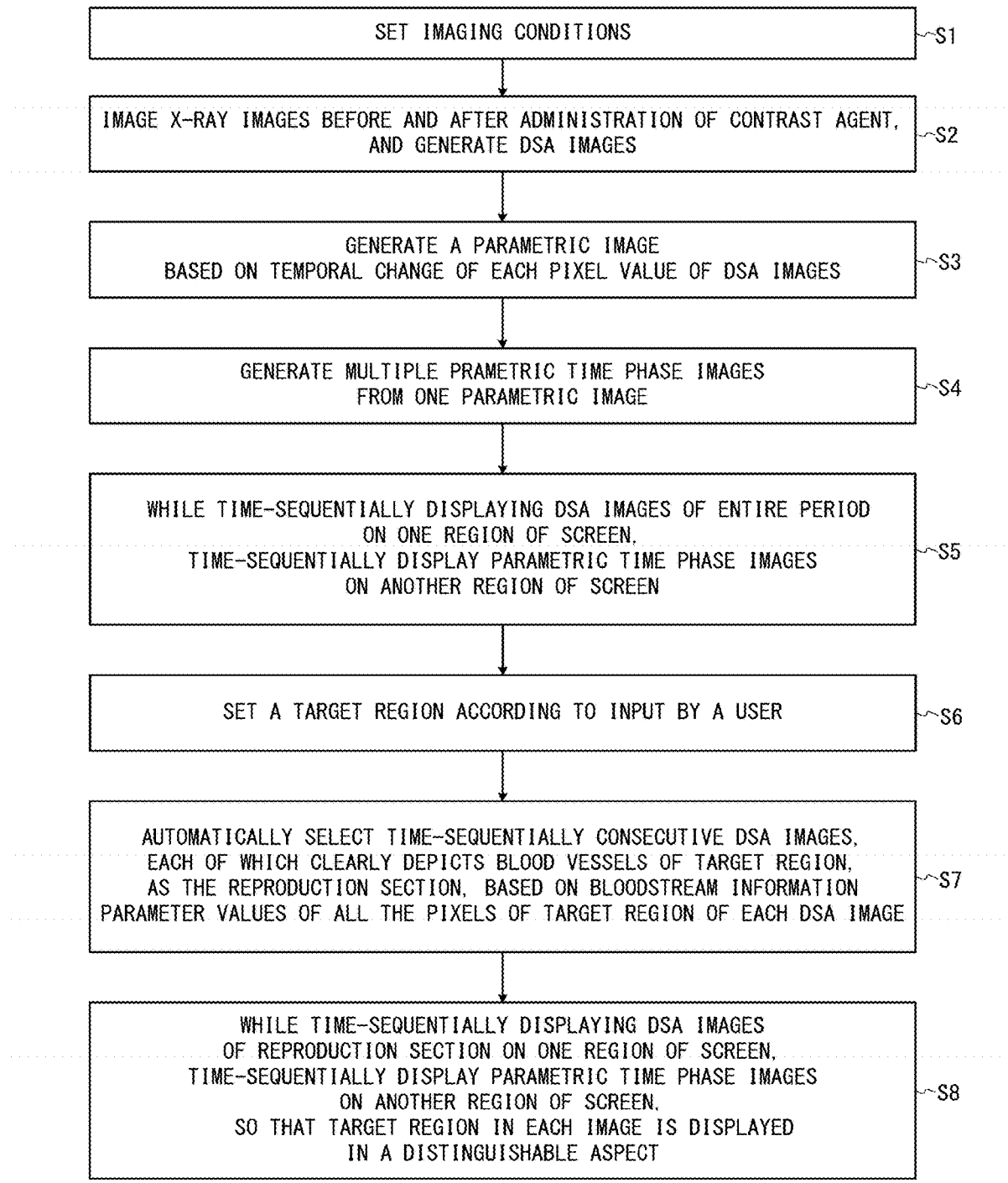
FIG. 14 is a flowchart showing an example of an imaging operation of the X-ray diagnostic apparatus of the present embodiment, when it is set to a target-region manual setting mode.

FIG. 14 is a flowchart showing an example of an imaging operation of the X-ray diagnostic apparatus 10 of the present embodiment, when it is set to the target-region manual setting mode. As to an example of an imaging operation in the case of automatically setting a target region, it will be explained in the next FIG. 15. Hereinafter, according to the step numbers in the flowchart shown in FIG. 14, an imaging operation of the X-ray diagnostic apparatus 10 in the target-region manual setting mode will be explained by referring to the above-described FIG. 1 to FIG. 13 as required.

[Step S1] The system control unit 42a (FIG. 1) sets all the imaging conditions at each time phase before and after administration of contrast agent, based on some imaging conditions inputted via the input circuit 48 such as an imaging region, a tube current, a tube voltage and X-ray pulse width.

Afterward, the processing proceeds to the Step S2.

[Step S2] Before and after administration of contrast agent, projection data of time-sequential X-ray images on the same region of the same object P are generated by a conventionally known imaging operation.

Specifically, before administration of contrast agent, the high-voltage generator 31 supplies the X-ray tube 34 with high voltage under the control of the system control unit 42a, the X-ray tube 34 generates X-rays, and the irradiation region of X-rays onto the object P is controlled by the diaphragm device 35.

The X-ray detector 36 converts X-rays having passed through the object P into electric signals, and outputs the electric signals to the projection data generation unit 42b.

The projection data generation unit 42b generates projection data of an X-ray image (i.e., a mask image) from the inputted electric signals. The projection data generation unit 42b outputs the generated projection data to the DSA image generation unit 42c and stores the generated projection data in the memory circuit 44.

Afterward, while positions of the table 22 and the C-arm 33 are fixed, contrast agent is administered to the object P by remote control of the contrast agent administration device 200 and then X-ray images (i.e., contrast images) for the same imaging region as the mask image are imaged at plural timings in a similar manner as described above. Afterward, projection data of the contrast images are inputted to the DSA image generation unit 42c and stored in the memory circuit 44.

In this manner, projection data of multiple time phases are generated for the same region of the same object P before and after the administration of contrast agent, so that luminance of each pixel becomes the level based on dose of the corresponding X-ray detection element of the X-ray detector 36. The DSA image generation unit 42c generates image data of time-sequential DSA images of multiple time phases based on the projection data of the mask image and the contrast images, and stores the generated image data of time-sequential DSA images in the memory circuit 44.

Afterward, the processing proceeds to the Step S3.

[Step S3] The bloodstream image acquisition unit 46a of the image processing device 46 acquires the image data of time-sequential DSA images of multiple time phases from the memory circuit 44, stores the acquired image data, and outputs the acquired image data to the derivative image generation unit 46b. The derivative image generation unit 46b generates image data of one parametric image, by calculating time phase change (temporal change) of pixel values of each pixel at the same position through all the DSA images as explained with FIG. 2 and FIG. 3.

Afterward, the processing proceeds to the Step S4.

[Step S4] The derivative image generation unit 46b generates image data of parametric time phase images of at least one cycle from the image data of one parametric image generated in the Step S3. The methods of generating parametric time phase images have been already explained with FIG. 4 and FIG. 5.

In consideration of the following three points here, it is desirable that the derivative image generation unit 46b determines the number of parametric time phase images to be generated for one cycle according to the number of all the time phases of DSA images, for example.

Firstly, DSA images in which blood flow of the target region is clearly depicted are generally only several percent of the DSA images of all the time phases in many cases.

Secondly, if the frame rate of consecutively displaying parametric time phase images is too faster than the frame rate of the DSA images of the reproduction section, it only leads to increase in computation load of generating image data.

Thirdly, if the number of parametric time phase images for one cycle is too small, the frame rate of the parametric time phase images becomes so slow compared with the frame rate of consecutively displaying the DSA images of the reproduction section that an observer feels unnatural in comparative observation between both images.

For example, consider a case where the derivative image generation unit 46b generates parametric time phase images, whose number is ten percent of the number of the DSA images of all the time phases, for one cycle of the circular color-assignment table data. In this case, if parametric time phase images of one cycle are reproduced in the display period of the DSA images of the reproduction section, the possibility that the frame rate of the parametric time phase images becomes close to the frame rate of the DSA images is high. If the frame rate of the parametric time phase images is close to the frame rate of the DSA images, natural moving picture display can be achieved in comparative observation between both images.

After generating parametric time phase images, the processing proceeds to the Step S5.

[Step S5] The display control unit 46e acquires the image data of the DSA images of all the time phases from the bloodstream image acquisition unit 46a, transfers the acquired data to the display 47. Then, the display control unit 46e controls the display 47, so that each of the DSA images of all the time phases is time-sequentially and consecutively displayed on one region of its screen such as the upper half or the lower half thereof. At the same time, the display control unit 46e acquires image data of parametric time phase images of at least one cycle from the derivative image generation unit 46b, transfers the acquired data to the display 47, and controls the display 47 so that each of the parametric time phase images is time-sequentially and consecutively displayed on another region of its screen such as the lower half or the upper half thereof.

Afterward, the processing proceeds to the Step S6.

[Step S6] While observing each parametric time phase image on the display 47, a user selects a target region on the displayed parametric time phase image by operating the input circuit 48 with a non-illustrated mouse to enter the information of the target region such as region designation, two points designation, and one point designation, for example.

The target region setting unit 46c sets the target region on a parametric time phase image according to information on the target region inputted by a user, and outputs the positional information of the determined target region to the reproduction section selection unit 46d and the display control unit 46e.

Incidentally, the target region setting unit 46c commonly sets the region whose position is the same as the target region selected on the parametric time phase image to every DSA image as the target region. Since image size is common to every DSA image and every parametric time phase image, positioning between DSA images and parametric time phase images is unnecessary in the processing of setting the target region to the DSA images. However, even if a parametric image and parametric time phase images are generated by downsizing each DSA image in terms of pixel number, the target region is commonly set to every DSA image so that the region of the object P depicted in the target region of every DSA image matches the region of the object P depicted in the target region of every parametric time phase image.

Afterward, the processing proceeds to the Step S7.

[Step S7] The reproduction section selection unit 46d acquires a bloodstream information parameter value of each pixel in the target region. Then, the reproduction section selection unit 46d selects DSA images between two time phases corresponding to the respective minimum and maximum values of the bloodstream information parameter values in the target region as the reproduction section, for example. In other words, the reproduction section selection unit 46d selects the reproduction section by selecting at least two DSA images corresponding to these two time phases.

The reproduction section selection unit 46d outputs information on the selected reproduction section to the display control unit 46e. In addition, the reproduction section selection unit 46d may output information on image data selected for selecting the reproduction section, so as to store this information in the memory circuit 44, an image processing server of a PACS (Picture Archiving and Communication System), and the like. Details of methods of automatically selecting a reproduction section have been already explained by reference to FIG. 8.

As mentioned above, a reproduction section may be selected by using another bloodstream information parameter which changes according to bloodstream arrival time such as TTP, instead of TTA values of all the pixels in a target region. In addition, consecutive DSA images of an interval, which is slightly expanded from the interval between two time phases corresponding to the respective minimum and maximum values of bloodstream information parameter values, may be selected as the reproduction section as mentioned above.

Afterward, the processing proceeds to the Step S8.

[Step S8] The display control unit 46e performs image processing on the image data of each DSA image of the reproduction section, so that the target region in each DSA image is displayed with a distinguishable aspect. In addition, the display control unit 46e performs image processing on the image data of each parametric time phase image inputted from the derivative image generation unit 46b, so that the target region in each parametric time phase image is displayed with a distinguishable aspect.

The display control unit 46e outputs the image data of each DSA image of the reproduction section, in which the display aspect of the target region is changed into a distinguishable aspect, to the display 47. The display control unit 47 also outputs the image data of each parametric time phase images, in which the display aspect of the target region is changed into a distinguishable aspect, to the display 47.

Afterward, under the control of the display control unit 46e, the display 47 time-sequentially displays the DSA images of the reproduction section in one region of its screen so that the target region is displayed with a distinguishable aspect, while time-sequentially displaying the parametric time phase images on another region of its screen. Details of the above display methods have been already explained by reference to FIG. 9 to FIG. 13.

The foregoing is the explanation of the flow of FIG. 14, and the following two points are supplemented.

Firstly, the execution timing of the processing from the Steps S5 to S8 is not limited to timing after completion of postoperative fluoroscopic imaging before and after administration of contrast agent. In other words, it is not limited to the timing after t=5" in the example of each top part in FIG. 6 and FIG. 7. The processing from the Steps S5 to S8 may be executed after preoperative imaging and before the operative treatment in order to, for example, finally confirm the position of the therapeutic region. In the example of each top part in FIG. 6 and FIG. 7, the processing from the Steps S5 to S8 may be executed in the interval between t=5 and t=0'. Additionally, the processing from the Steps S5 to S8 may be executed after imaging during operative treatment is once completed, i.e., the interval between t=5' and t=0" in the example of each top part in FIG. 6 and FIG. 7. Thus, fluoroscopic imaging in the Step S2 in FIG. 14 may be performed (a) only before operative treatment, (b) before operative treatment and during operative treatment, or (c) before operative treatment, during operative treatment, and after operative treatment, for example.

Secondly, since the processing of the Step S2 presupposes fluoroscopic imaging as an example here, vertical pixel number and horizontal pixel number are common to all the DSA images. Therefore, vertical pixel number and horizontal pixel number of each of parametric image and parametric time phase images derivatively generated from DSA images are the same as those of the original DSA images. Thus, the target region being commonly set to all the DSA images is also commonly set to a parametric image and all the parametric time phase images without causing positional displacement.

Next, a case where the X-ray diagnostic apparatus 10 is set to the target region automatic setting mode will be explained.

Figure 15:
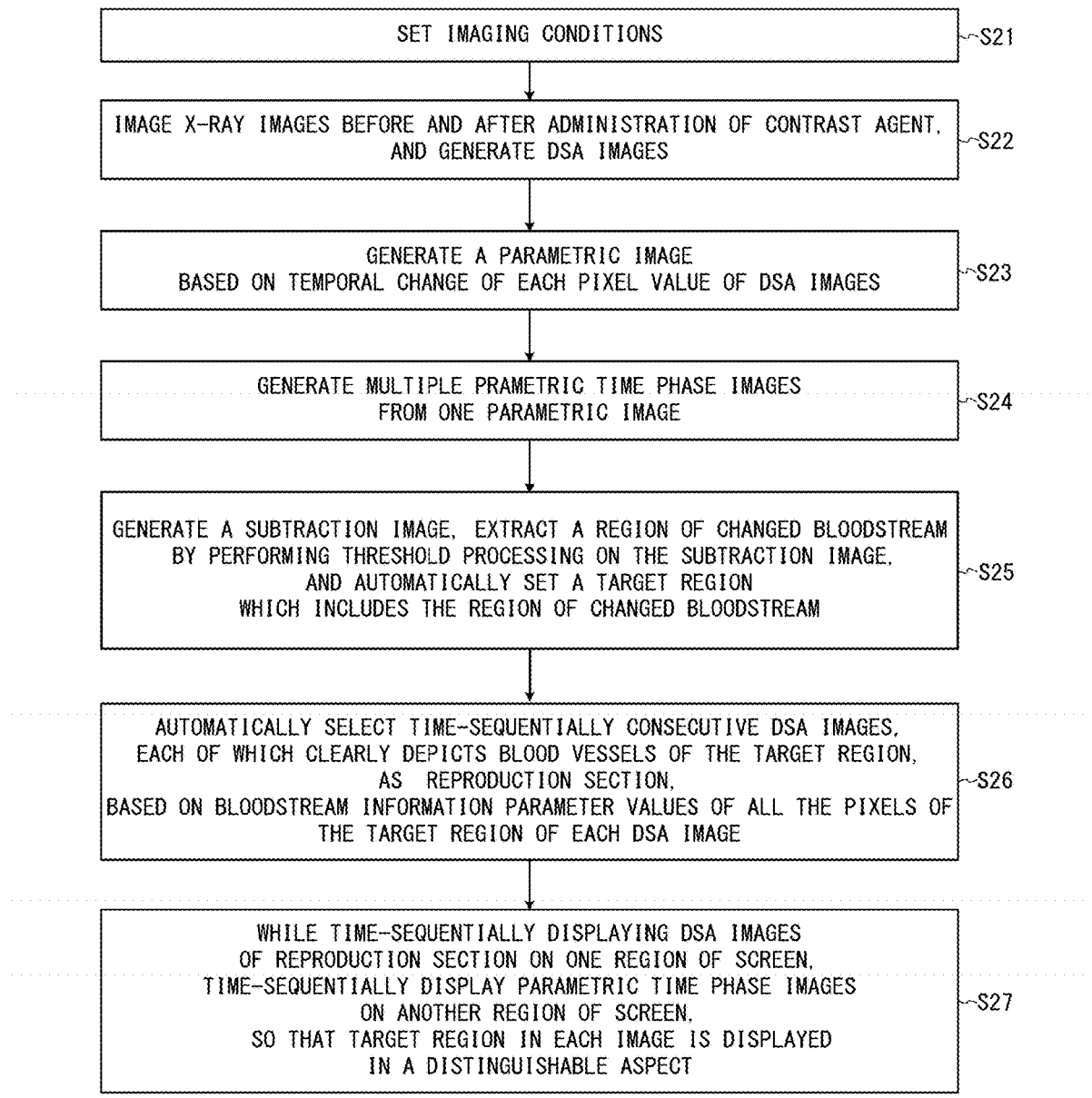
FIG. 15 is a flowchart showing an example of an imaging operation of the X-ray diagnostic apparatus of the present embodiment, when it is set to a target-region automatic setting mode.

FIG. 15 is a flowchart showing an example of an imaging operation of the X-ray diagnostic apparatus 10 of the present embodiment, when it is set to the target-region automatic setting mode. Hereinafter, according to the step numbers in the flowchart shown in FIG. 15, an imaging operation of the X-ray diagnostic apparatus 10 in the target region automatic setting mode will be explained by reference to the above-described FIG. 1 to FIG. 14 as required.

[Steps S21 to S24] The processing from the Steps S21 to S24 is similar to the processing from the Steps S1 to S4 in FIG. 14, and duplicate explanation is omitted.

Afterward, the processing proceeds to the Step S25.

[Step S25] The target region setting unit 46c extracts a region of changed bloodstream by, for example, performing threshold processing on the subtraction image between the parametric image before the operative treatment and the parametric image after the operative treatment. Then, the target region setting unit 46c calculates the minimum rectangular region in which the extracted region of changed bloodstream is included as the target region, for example. The target region setting unit 46c sets the target region on the color image (i.e. on the parametric time phase images in this example). Note that this is only one example of methods of automatically setting a target region, and the details have been already explained with FIG. 6 and FIG. 7.

After the target region is automatically set by the target region setting unit 46c, the processing proceeds to the Step S26.

[Steps S26 and S27] The processing in the Steps S26 and S27 is similar to the processing in the Steps S7 and S8 in FIG. 14, and duplicate explanation is omitted.

The foregoing is the explanation of the imaging operations of the X-ray diagnostic apparatus 10 of the present embodiment.

Effects of the Present Embodiment

DSA images in which blood flow of a target region is clearly depicted are, for example, only several percent of the DSA images of all the time phases. However, configuration, in which an observer is required to select a reproduction section from the DSA images of all the time phases, involves complicated manipulation for an observer.

For the above reason, DSA images of a reproduction section are automatically selected by the reproduction section selection unit 46d of the image processing device 46 in the X-ray diagnostic apparatus so as to include DSA images each of which clearly depicts blood flow of the target region in the present embodiment (see the Step S7 in FIG. 14 and the Step S26 in FIG. 15).

As to the above-described automatic selection of a reproduction section, for example, DSA images between two time phases corresponding to the respective minimum and maximum values of a bloodstream information parameter inside the target region. Thus, DSA images each of which clearly depicts blood flow of the target region can be infallibly selected (see FIG. 8).

Then, since the DSA images of only the reproduction section are time-sequentially displayed on one region of the screen of the display 47, an observer can visually and efficiently confirm blood flow in the target region.

Moreover, in the present embodiment, parametric time phase images are time-sequentially displayed on another region of the screen of the display 47 in parallel with time-sequential display of the DSA images of the reproduction section. Since a series of parametric time phase images has an advantage of enabling an observer to visually follow not only blood flow of the target region but also blood flow of the entire image by continuous color change, an observer can visually and easily discriminate blood flow by comparison between DSA images and parametric time phase images.

Furthermore, since the target region is distinguishably displayed in parallel display of the DSA images of the reproduction section and the parametric time phase images as explained by reference to FIG. 9 to FIG. 13, visibility of the currently reproduced target region improves. As a result, an observer can visually distinguish the blood flow in the target region more easily.

According to the above-described embodiment, it can be acquired a blood vessel image in which a blood vessel, via which the contrast agent flows into a lesion area, can be clearly distinguished from other blood vessels.

Supplementary Notes on Embodiments

[1] In each of the above-described embodiments, an example in which the DSA image generation unit 42c generates image data of DSA images and (the bloodstream image acquisition unit 46a of) the image processing device 46 acquires projection data of respective X-ray images before and after administration of contrast agent from the memory circuit 44 has been explained. However, embodiments of the present invention are not limited to such an aspect. For example, the X-ray diagnostic apparatus 10 may be configured so that the DSA image generation unit 42c is disposed not inside the imaging control device 42 but inside the image processing device 46 and generates image data of DSA images in a similar manner.

[2] If blood flow is depicted to a certain degree in time-sequential contrast images after administration of contrast agent, contrast images may be used as bloodstream images instead of DSA images. In other words, a target region may be set to a contrast image at each imaging time manually or automatically as described above, and contrast images each of which clearly depicts blood flow of the target region may be selected as the reproduction section in a similar manner as described above. In this case, time-sequential reproduction of the contrast images of the reproduction section on one region of the screen of the display 47 and time-sequential reproduction of parametric time phase images on another region of the screen are executed in parallel by displaying the common target region with a distinguishable aspect in a similar manner as described above.

[3] In each of the above-described embodiments, an example in which the image processing device 46 is installed in the X-ray diagnostic apparatus 10 has been explained. However, embodiments of the present invention are not limited to such an aspect. The image processing device 46 may be installed in another image diagnosis apparatus capable of imaging bloodstream images before and after administration of contrast agent such as an X-ray CT (Computed Tomography) apparatus and a magnetic resonance imaging apparatus, for example.

[4] In each of the above-described embodiments, an example in which respective composite images and the like are displayed on the display 47 connected to the image processing device 46 by the display control function of the reproduction section selection unit 46d has been explained. However, embodiments of the present invention are not limited to such an aspect. The display 47 may be configured as one component of the image processing device 46.

[5] An image processing program may be generated by coding the processing from the Steps S3 to S8 in FIG. 14. The image processing device 46 in FIG. 1 may be interpreted as a device in which such an image processing program is installed. As to the processing from the Steps S23 to S27 in FIG. 15, an image processing program may be generated in a similar manner as described above.

Although the imaging control device 42 and the image processing device 46 are explained as hardware in FIG. 1, each of the imaging control device 42 and the image processing device 46 may be configured as processing circuitry which includes at least one processor and one memory circuit.

In this case, the image processing device 46 implements the bloodstream image acquisition function (46a), the derivative image generation function (46b), the target region setting function (46c), the reproduction section selection function (46d), and the display control function (46e), by executing programs stored in the memory circuit of the processing circuitry. Each of the above-described functions is stored in the form of a program in the memory circuit. The same holds true for the imaging control device 42.

The processing circuitry of the image processing device 46 of the above-described embodiments is an example of the processing circuitry described in the claims.

The above-described term "processor" means, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in the memory circuit and executing the programs.

In addition, programs may be directly installed in the circuit of the processor instead of storing programs in the memory circuit. In this case, the processor implements various types of functions by reading out programs stored in its own circuit and executing the programs.

Moreover, each function may be implemented by processing circuitry configured of a single processor. Further, the processing circuitry may be configured by combining plural processors independent of each other so that each function of the processing circuitry is implemented by causing each processor to execute the corresponding program.

When plural processors are provided for the processing circuitry, a memory circuit for storing the programs may be provided for each processor or one memory circuit may collectively store all the programs corresponding to all the processors.

[6] In the above-described embodiment, an example of parallel display of DSA images and parametric time phase images as two-dimensional images has been explained. However, embodiments of the present invention are not limited to such an aspect. For example, consider a case where the image processing device 46 is installed in an image processing server of a PACS (Picture Archiving and Communication System) and acquires multiple of time-sequential volume data of the same region of the same object P before and after administration of contrast agent imaged by an image diagnostic apparatus such as an X-ray CT (Computed Tomography) apparatus.

In this case, the display 47 may be configured as a naked eye stereoscopic display device. This is so that each of the three-dimensional DSA images of the reproduction section and each of the three-dimensional parametric time phase images can be stereoscopically displayed in parallel with the target region displayed in a distinguishable aspect by three-dimensionally performing processing similar to the above-described embodiment, for example.

Specifically, volume data of DSA images of the respective time phases are generated by subtracting the volume data of the three-dimensional mask image from the volume data of a three-dimensional contrast image of each imaging time. Next, image data of a two-dimensional DSA image of a certain time phase γ are generated based on each pixel value of the central cross-section of the volume data of the DSA image of the time phase γ, for example.

Then, two-dimensional parallax images of the time phase γ are generated, on the basis of the two-dimensional DSA image of the time phase γ and the depth information obtained from pixel values of all the cross-sections of the volume data of the DSA image of the time phase γ. By treating these two-dimensional parallax images as one set, the image data of the DSA image of the time phase γ for stereoscopic display can be generated.

As to DSA images of other time phases, the image data for stereoscopic display can be generated in a similar manner as described above. As to parametric time phase images, their image data for stereoscopic display can be generated in a similar manner as described above. As to methods of generating parallax images and configuration of a naked eye stereoscopic display device, for example, conventional technology described in Japanese Patent Application Laid-open Publication No. 2007-94022 may be used.

[7] Correspondences between terms used in the claims and terms used in the embodiment described above will be described. Note that the correspondence described below is possible interpretation for reference and should not be construed as limiting the present invention.

The entirety of the bed device 20, the X-ray generation/detection system 30, and the imaging control device 42 which generates projection data of X-ray images and image data of DSA images by performing X-ray imaging on an object is an example of the X-ray imaging device described in the claims.

[8] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An image processing device, comprising:
processing circuitry configured to
acquire a plurality of first image data indicating a plurality of time-sequential bloodstream images obtained after administering contrast agent to an object,
setting a target region on second image data, the second image data being generated based on the plurality of first image data so as to indicate information on temporal change of pixel values of each pixel, and
select a reproduction section by selecting at least reproduction-start image data and reproduction-end image data from the plurality of first image data based on bloodstream information of the target region.

2. The image processing device according to claim 1, wherein the processing circuitry is configured to select image data of consecutive time-sequential bloodstream images including the reproduction-start image data and the reproduction-end image data out of the plurality of first image data as the reproduction section based on the bloodstream information of the target region.

3. The image processing device according to claim 1, wherein the processing circuitry is configured to output information on image data selected for selecting the reproduction section and store the information on image data selected for selecting the reproduction section in a memory circuit.

4. The image processing device according to claim 1, wherein the processing circuitry is configured to set at least two points on the second image data and set the target region based on the at least two points.

5. The image processing device according to claim 1, wherein the processing circuitry is configured to generate the second image data as color image data based on the plurality of time-sequential bloodstream images.

6. The image processing device according to claim 1, wherein the plurality of first image data are projection data of a plurality of time-sequential X-ray images obtained after administering contrast agent to the object or image data of a plurality of time-sequential DSA images obtained from the projection data of a plurality of time-sequential X-ray images.

7. The image processing device according to claim 1, wherein the processing circuitry is configured to consecutively display a plurality of bloodstream images included in the reproduction section in time-sequential order on a display connected with the image processing device.

8. The image processing device according to claim 7, wherein the processing circuitry is configured to cause the display to perform enlarged display of the target region without displaying regions, other than the target region, in each of the plurality of bloodstream images.

9. The image processing device according to claim 7, wherein the processing circuitry is configured to
acquire image data of a plurality of time-sequential DSA images as the plurality of first image data,
calculate temporal change of pixel values for each pixel whose position is common to time-sequential DSA images,
calculate a bloodstream information parameter value for each pixel based on the temporal change of pixel values,
generate image data of a plurality of time-sequential parametric time phase images as the second image data by assigning a pattern of chromatic colors to the each pixel, the pattern of chromatic colors changing for every time phase according to the bloodstream information parameter value, and
control the display in such a manner that the display consecutively displays a plurality of DSA images included in the reproduction section in time-sequential order on one region of a screen of the display while the display consecutively displays the plurality of time-sequential parametric time phase images on another region of the screen.

10. The image processing device according to claim 9, wherein the processing circuitry is configured to generate the image data of the plurality of time-sequential parametric time phase images, by aligning a length of one cycle of the pattern of chromatic colors over every pixel, and
control a frame rate of reproducing the plurality of time-sequential parametric time phase images such that a period of consecutively displaying all of the DSA images included in the reproduction section in time-sequential order is synchronized with a period of consecutively displaying one cycle of the plurality of time-sequential parametric time phase images in time-sequential order.

11. The image processing device according to claim 9, wherein the processing circuitry is configured to
generate the image data of the plurality of time-sequential parametric time phase images, by aligning a length of one cycle of the pattern of chromatic colors over every pixel, and
control a frame rate of reproducing the plurality of time-sequential parametric time phase images such that a period of consecutively displaying all of the DSA images included in the reproduction section in time-sequential order is synchronized with a period of consecutively displaying a plurality of cycles of the plurality of time-sequential parametric time phase images in time-sequential order.

12. The image processing device according to claim 7, wherein the processing circuitry is configured to distinguishably display the target region on the display by covering regions except the target region with a fixed color or superimposing a frame on an outer border of the target region.

13. The image processing device according to claim 1, wherein the processing circuitry is configured to receive inputted information on the target region and set the target region according to the inputted information on the target region.

14. The image processing device according to claim 1, wherein the processing circuitry is configured to perform threshold processing on a subtraction image acquired by subtraction between the plurality of time-sequential bloodstream images, and set the target region based on a result of the threshold processing.

15. An X-ray diagnostic apparatus, comprising:

an X-ray generator configured to generate X-rays;

an X-ray detector configured to detect the X-rays having passed through the object;

control circuitry configured to generate the plurality of first image data based on the detected X-rays having passed through the object, at a corresponding plurality of times after administration of contrast agent to the object; and the image processing device according to claim 1.

* * * * *